(12) United States Patent
Pellegrini

(10) Patent No.: US 11,893,663 B2
(45) Date of Patent: Feb. 6, 2024

(54) CONFIDENCE MAP GENERATION FOR SEGMENTED OPTICAL COHERENCE TOMOGRAPHIC DATA

(71) Applicant: OPTOS PLC, Dunfermline (GB)

(72) Inventor: Enrico Pellegrini, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 484 days.

(21) Appl. No.: 17/218,480

(22) Filed: Mar. 31, 2021

(65) Prior Publication Data
US 2022/0319070 A1  Oct. 6, 2022

(51) Int. Cl.
*G06T 11/00* (2006.01)
*A61B 3/10* (2006.01)
*A61B 3/12* (2006.01)
*G06F 18/2431* (2023.01)
*G06T 7/143* (2017.01)
*G06T 7/11* (2017.01)

(52) U.S. Cl.
CPC ............ *G06T 11/008* (2013.01); *A61B 3/102* (2013.01); *A61B 3/12* (2013.01); *G06F 18/2431* (2023.01); *G06T 7/11* (2017.01); *G06T 7/143* (2017.01); *G06T 2207/10101* (2013.01); *G06T 2207/20076* (2013.01); *G06T 2207/30041* (2013.01)

(58) Field of Classification Search
CPC ......... G06T 11/008; G06T 7/11; G06T 7/143; G06T 2207/10101; G06T 2207/20076; G06T 2207/30041; A61B 3/102; A61B 3/12; G06F 18/2431
See application file for complete search history.

(56) References Cited

FOREIGN PATENT DOCUMENTS

EP  3596697 B1 *  3/2021  ........... G06K 9/4628

OTHER PUBLICATIONS

Grading Diabetic Retinopathy from Stereoscopic Color Fundus Photographs—An Extension of the Modified Airlie House Classification, ETDRS Report No. 10, Ophthalmology, vol. 98, Issue 5, Supplement, 786-806, May 1, 1991.

\* cited by examiner

*Primary Examiner* — Edward F Urban
*Assistant Examiner* — Ashley L. Hytrek
(74) *Attorney, Agent, or Firm* — FAEGRE DRINKER BIDDLE & REATH

(57) ABSTRACT

A method of generating a segmentation confidence map by processing classification values each indicating a respective classification of a respective voxel of a retinal C-scan into a respective retinal layer class of a predefined set of retinal layer classes, the method comprising: generating, for each voxel, a respective confidence value which indicates a level of confidence in the classification of the voxel; for a retinal layer class of the predefined set, identifying a subset of the voxels such that the classification value generated for each voxel indicates a classification of the voxel into the retinal layer class; calculating, for each A-scan having voxels in the identified subset, a respective average of the confidence indicator values generated for the voxels; and using the calculated averages to generate the map, which indicates a spatial distribution of a level of confidence in the classification of the voxels.

25 Claims, 15 Drawing Sheets

… (1) …

CONFIDENCE MAP GENERATION FOR SEGMENTED OPTICAL COHERENCE TOMOGRAPHIC DATA

TECHNICAL FIELD

Example aspects herein generally relate to the field of Optical Coherence Tomography (OCT) data processing and, more particularly, to a technique for generating a confidence map for a retinal layer segmentation of an OCT volumetric scan of a retina of an eye.

BACKGROUND

Optical coherence tomography provides a powerful tool for examining and assessing the health of the retina of an eye. Being able to automatically and accurately map out or trace, across an OCT image of the retina, a specific retinal layer of interest from among the different layers of the retina that are discernible in the OCT image, would greatly facilitate OCT image analysis and may allow useful information on the retina to be obtained.

FIGS. 1a and 1b (from "Atlas of OCT" by Adams, N. A., Heidelberg Engineering) illustrate an example OCT B-scan image of a retina (FIG. 1a), and an enlarged segment (FIG. 1b) of the OCT B-scan image. A grey-scale enhancement of the enlarged segment is shown on the left-hand side of FIG. 1b. Up to 18 distinct layers are typically visible in an OCT B-scan image of a retina, and a mapping of some of these layers to associated anatomical layers of the retina (including the Inner/Outer Segment (IS/OS junction layer)) is shown in FIG. 1b.

Various kinds of image classification algorithm have been used to automatically segment an OCT retinal image into distinct retinal layers. A review of such algorithms is provided in "A Review of Algorithms for Segmentation of Optical Coherence Tomography from Retina" by R. Kafieh et al, J Med Signals Sens. 2013 January-March; 3(1): 45-60.

SUMMARY

There is provided, in accordance with a first example aspect herein, a computer-implemented method of generating a segmentation confidence map by processing retinal layer segmentation data generated by a retinal layer segmentation algorithm, which generates, as the retinal layer segmentation data, a respective set of probability values for each voxel of at least a portion of a C-scan of a retina, wherein each probability value indicates a probability of the voxel belonging to a respective retinal layer class of a predefined set of retinal layer classes. The method comprises generating, for each voxel of a set of voxels for which the retinal layer segmentation data has been generated: a respective value of a classification indicator based on the respective set of probability values, the value of the classification indicator indicating a classification of the voxel as belonging to a respective retinal layer class of the predefined set of retinal layer classes; and a respective value of a first confidence indicator which is indicative of a respective level of confidence in the classification of the voxel. The method further comprises: identifying, for a retinal layer class of the predefined set of retinal layer classes, a subset of the set of voxels such that the value of the classification indicator generated for each voxel of the subset indicates a classification of the voxel as belonging to the retinal layer class; calculating, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and generating the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

In the generating of a respective value of the first confidence indicator for each voxel of the set of voxels, the respective value of the first confidence indicator may be generated based on the respective set of probability values. The respective value of the first confidence indicator may be calculated for each voxel of the set of voxels as one of: a standard deviation of the respective set of probability values; $1-D$, where D is a difference between a highest probability value in the respective set of probability values and a lowest probability value in the respective set of probability values; and $1-P$, where P is a difference between a highest probability value in the respective set of probability values and a second highest probability value in the respective set of probability values.

The retinal layer segmentation algorithm may comprise one of a convolutional neural network (CNN), a Gaussian Mixture model, a Random Forest, a Bayesian classifier and a Support Vector Machine.

The retinal layer segmentation algorithm may generate the retinal layer segmentation data by calculating, for each voxel of the at least a portion of the C-scan, a respective set of probability values, wherein each probability value indicates a probability of the voxel belonging to a respective class of a predefined set of classes, the predefined set of classes comprising the predefined set of retinal layer classes and a predefined background class. The value of the classification indicator generated for each voxel of the set of voxels may indicate a classification of the voxel as belonging to a respective class of the predefined set of classes. The method may further comprise: for the background class, identifying a second subset of the set of voxels such that the value of the classification indicator generated for each voxel of the second subset indicates a classification of the voxel as belonging to the background class; calculating, for each A-scan of a plurality of A-scans of the C-scan, which A-scan has at least one voxel in the identified second subset, a respective value of the second confidence indicator, based on at least one value of the first confidence indicator that has been respectively generated for the at least one voxel in the A-scan; and generating a second segmentation confidence map using the values of the second confidence indicator calculated for the A-scans having at least one voxel in the identified second subset, such that the second segmentation confidence map indicates a spatial distribution of a level of confidence in the classification of the voxels in the second subset as belonging to the background class.

There is provided, in accordance with a second example aspect herein, a computer-implemented method of generating a segmentation confidence map by processing retinal layer segmentation data generated by a retinal layer segmentation algorithm, which generates the retinal layer segmentation data by calculating, for each voxel of at least a portion of a C-scan of a retina, a respective value of a classification indicator indicating a classification of the voxel as belonging to a retinal layer class of the predefined set of retinal layer classes. The method comprises: generating, for each voxel of a set of voxels for which the retinal layer segmentation data has been generated, a respective value of a first confidence indicator which is indicative of a level of confidence in the classification of the voxel; identifying, for a retinal layer class of the predefined set of retinal layer classes, a subset of the set of voxels such that the value of the classification indicator generated for each voxel of the subset indicates a classification of the voxel as belonging to the retinal layer class; calculating, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and generating the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

In the generating of a respective value of the first confidence indicator for each voxel of the set of voxels, the respective value of the first confidence indicator may be generated using a value of a local image quality metric that indicates an image quality of a region of an image, which region has been rendered from a part of the C-scan comprising the voxel.

Any of the computer-implemented methods set out above may further comprise using the segmentation confidence map and the values of the classification indicator to determine an indication of a thickness of a layer of the retina associated with the retinal layer class.

The indication of the thickness of the layer of the retina may be determined by a process of: using the segmentation confidence map to identify, in the plurality of A-scans, an A-scan for which the value of a second confidence indicator is indicative of a level of confidence in the classification of the at least one voxel in the A-scan into the retinal layer class that exceeds a predefined threshold; and determining a count of the at least one voxel in the identified A-scan. This process may be repeated to: identify, using the segmentation confidence map, a second plurality of A-scans in the plurality of A-scans, wherein the respective value of a second confidence indicator calculated for each A-scan of the second plurality of A-scans is indicative of a respective level of confidence in the classification of the at least one voxel in the A-scan into the retinal layer class that exceeds the predefined threshold; and determine, for each A-scan of the identified second plurality of A-scans, a respective count of the at least one voxel in the A-scan, wherein a respective indication of the thickness of the layer of the retina is determined for each predefined region of a plurality of predefined regions of the retina, from which predefined region a respective set of A-scans of the identified second plurality of A-scans has been acquired, by calculating an average of the counts determined for the A-scans of the set of A-scans. The predefined regions may be demarcated by an Early Treatment Diabetic Retinopathy Study (ETDRS) grid.

Alternatively, the indication of the thickness of the layer of the retina may be determined by: determining, for each A-scan of the plurality of A-scans, which A-scan has at least one voxel in the identified subset, a respective count of the at least one voxel in the identified subset in the A-scan; and determining a weighted average of the determined counts, wherein the respective count determined for each A-scan having at least one voxel in the identified subset is weighted by the respective value of the second confidence indicator. The indication of the thickness of the layer of the retina may be determined for each predefined region of a plurality of predefined regions of the retina by: determining, for each A-scan acquired from the predefined region, which A-scan has at least one voxel in the identified subset, a respective count of the at least one voxel in the identified subset in the A-scan; and determining a weighted average of the determined counts, wherein the respective count determined for each A-scan acquired from the predefined region and having at least one voxel in the identified subset is weighted by the respective value of the second confidence indicator. The predefined regions may be demarcated by an Early Treatment Diabetic Retinopathy Study (ETDRS) grid.

Any of the computer-implemented methods set out above may further comprise generating image data defining an image of at least a portion of the segmentation confidence map, and causing the image to be displayed on a display. The image may be caused to be displayed on the display as one of: an overlay on an en-face image displayed on the display, the en-face image being based on the subset of voxels classified as belonging to the retinal layer class; an overlay on a retinal layer thickness map displayed on the display, the retinal layer thickness map being based on the subset of voxels classified as belonging to the retinal layer class; and a plot aligned with a representation of a B-scan displayed on the display, the B-scan being based on the subset of voxels classified as belonging to the retinal layer class.

Any of the computer-implemented methods set out above may further comprise determining whether the segmentation confidence map indicates a level of confidence in the classification of the voxels in the subset as belonging to the retinal layer class of the predefined set of retinal layer classes that is below a confidence threshold and, in a case where the segmentation confidence map is determined to indicate a level of confidence in the classification of the voxels that is below the confidence threshold, generating an alert for a user.

There is also provided, in accordance with a third example aspect herein, a computer program comprising computer program instructions which, when executed by a computer, cause the computer to perform any of the methods set out above. The computer program may be stored on a non-transitory computer-readable storage medium, or it may be carried by a signal.

There is also provided, in accordance with a fourth example aspect herein, an apparatus for generating a segmentation confidence map by processing retinal layer segmentation data generated by a retinal layer segmentation algorithm, which generates, as the retinal layer segmentation data, a respective set of probability values for each voxel of at least a portion of a C-scan of a retina, wherein each probability value indicates a probability of the voxel belonging to a respective retinal layer class of a predefined set of retinal layer classes. The apparatus comprises a voxel classification module arranged to generate, for each voxel of a set of voxels for which the retinal layer segmentation data has been generated: a respective value of a classification indicator based on the respective set of probability values, the value of the classification indicator indicating a classification of the voxel as belonging to a respective retinal layer class of the predefined set of retinal layer classes; and a respective value of a first confidence indicator which is indicative of a respective level of confidence in the classification of the voxel. The apparatus further comprises: a voxel identification module arranged to identify, for a retinal layer class of the predefined set of retinal layer classes, a subset of the set of voxels such that the value of the classification indicator generated for each voxel of the subset indicates a classification of the voxel as belonging to the retinal layer class; a confidence evaluation module arranged to calculate, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and a segmentation confidence map generation module arranged to generate the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

There is also provided, in accordance with a fifth example aspect herein, an apparatus for generating a segmentation confidence map by processing retinal layer segmentation data generated by a retinal layer segmentation algorithm, which generates the retinal layer segmentation data by generating, for each voxel of at least a portion of a C-scan of a retina, a respective value of a classification indicator indicating a classification of the voxel as belonging to a retinal layer class of the predefined set of retinal layer classes. The apparatus comprises: a confidence indicator evaluation module arranged to generate, for each voxel of a set of voxels for which the retinal layer segmentation data has been generated, a respective value of a first confidence indicator which is indicative of a level of confidence in the classification of the voxel; a voxel identification module arranged to identify, for a retinal layer class of the predefined set of retinal layer classes, a subset of the set of voxels such that the value of the classification indicator generated for each voxel of the subset indicates a classification of the voxel as belonging to the retinal layer class; a confidence evaluation module arranged to calculate, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and a segmentation confidence map generation module arranged to generate the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

FIG. 1b shows an enlarged and partially enhanced segment of the OCT B-scan image of FIG. 1a.

DETAILED DESCRIPTION OF EXAMPLE EMBODIMENTS

Probabilistic models used for semantic segmentation of OCT C-scans, which include (but are not limited to) convolutional neural network (CNN) models, provide segmentation results that can be difficult to interpret, owing to a lack of information on a level of confidence that can be placed on the segmentation results. The inventor has recognised that probability information, which is used by probabilistic segmentation models to perform semantic segmentation but is then conventionally discarded, may be leveraged to provide an indication of a level of confidence in the segmentation results that can be used to enhance their interpretability, improve the reliability of retinal layer thickness measurements derived from the segmentation results, and provide metrics for logging OCT layer segmentation confidence, for example. Example embodiments which process probability information from a retinal layer segmentation algorithm to generate a segmentation confidence map that provides such an indication of a level of confidence in the segmentation results will now be described with reference to the figures.

First Example Embodiment

Figure 1A:
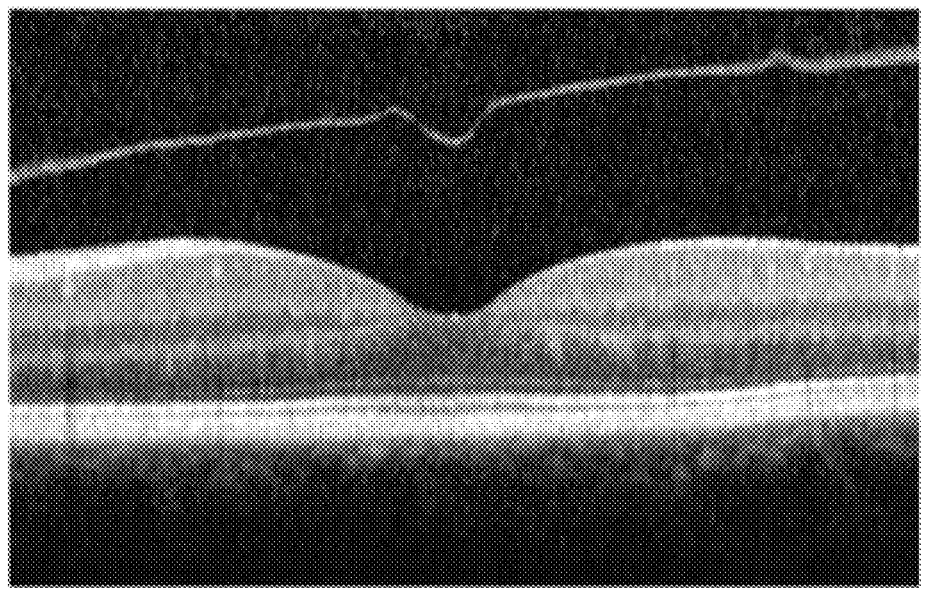
FIG. 1a illustrates an OCT B-scan image of a retina of an eye.
Figure 1B:
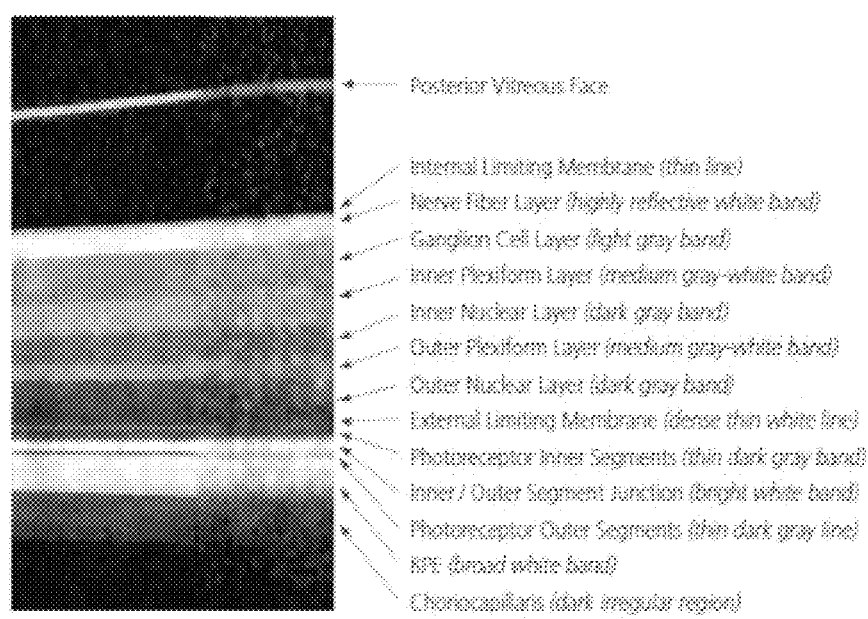

FIG. 1 is a schematic illustration of an apparatus 100 for generating a segmentation confidence map M by processing retinal layer segmentation data $D_{seg}$, which is generated by a retinal layer segmentation algorithm, RLSA. In the present example embodiment, the retinal layer segmentation algorithm processes a portion 20 of a C-scan 22 that has been acquired by an optical coherence tomography (OCT) imaging system to generate the retinal layer segmentation data $D_{seg}$, as illustrated schematically in FIG. 3. The C-scan 22 is a volumetric stack of n B-scans, where each B-scan is defined by a set of w×h voxels and can be rendered to provide a sectional view of the retina. Each B-scan is formed of a sequence of w A-scans, each A-scan being a one-dimensional array of h voxels whose values represent OCT measurement results taken at varying depths in the retina.

The OCT imaging system used to acquire the C-scan may be of any type known to those versed in the art, for example a point-scan OCT imaging system, which can acquire an OCT image by scanning a laser beam laterally across a region of the eye. The OCT imaging system may alternatively be a parallel acquisition OCT imaging system, such as Full-Field OCT (FF-OCT) or Line-Field OCT (LF-OCT), which may offer superior A-scan acquisition rates (up to tens of MHz) by illuminating an area or a line on the sample, rather than scanning a single spot across the eye. In FF-OCT, a two-dimensional region of the eye is illuminated at the same time and the lateral positions across the region are concurrently captured using a photodetector array such as a high-speed charge-coupled device (CCD) camera. Where the OCT imaging system is a Full-field OCT, it may take the form of a full-field time-domain OCT (FF-TD-OCT) or full-field swept-source OCT (FF-SS-OCT), for example. In FF-TD-OCT, the optical length of the reference arm can be varied during a scan in order to image regions at different depths in the eye. Each frame captured by the high-speed camera in FF-TD-OCT therefore corresponds to a slice of the eye at a respective depth within the eye. In FF-SS-OCT, the sample region is full-field illuminated using a swept light source that emits light whose wavelength varies over time. As the wavelength of the swept light source is swept over a range of optical wavelengths, a spectrogram correlating reflectivity information against optical wavelength can be generated by the high-speed camera for each camera pixel. Each frame captured by the camera therefore corresponds to reflectivity information for a single wavelength of the swept light source. Upon acquiring a frame for every wavelength of the swept light source, a C-scan of the region can be obtained by performing a Fourier transform on the samples of spectrograms generated by the camera. In line-field OCT (LF-OCT), a line of illumination may be provided to the sample and a B-scan may be acquired in the imaging process. Line-field OCT may be classified as line-field time-domain OCT (LF-TD-OCT), line-field swept-source OCT (LF-SS-OCT), or line-field spectral-domain OCT (LF-SD-OCT), for example.

The retinal layer segmentation algorithm may be any kind of algorithm for semantic segmentation which provides a probabilistic output to an m-class classification task. The retinal layer segmentation algorithm may take one of many different forms known to those skilled in the art, and may comprise a convolutional neural network (CNN), a Gaussian Mixture model, a Random Forest, a Bayesian classifier or a Support Vector Machine, for example. By way of an example, the retinal layer segmentation algorithm is a CNN with a soft-max activation function output layer and a cross-entropy loss function in the present example embodiment. Regardless of its specific form, the retinal layer segmentation algorithm generates retinal layer segmentation data $D_{seg}$ in the form of a respective set of m probability values for each voxel (as exemplified by voxel 10) in the portion 20 of the C-scan 22, where m is an integer greater than or equal to 2. Thus, the output of the retinal layer segmentation algorithm is a hypervolume of size w×n×h×m.

Figure 3:
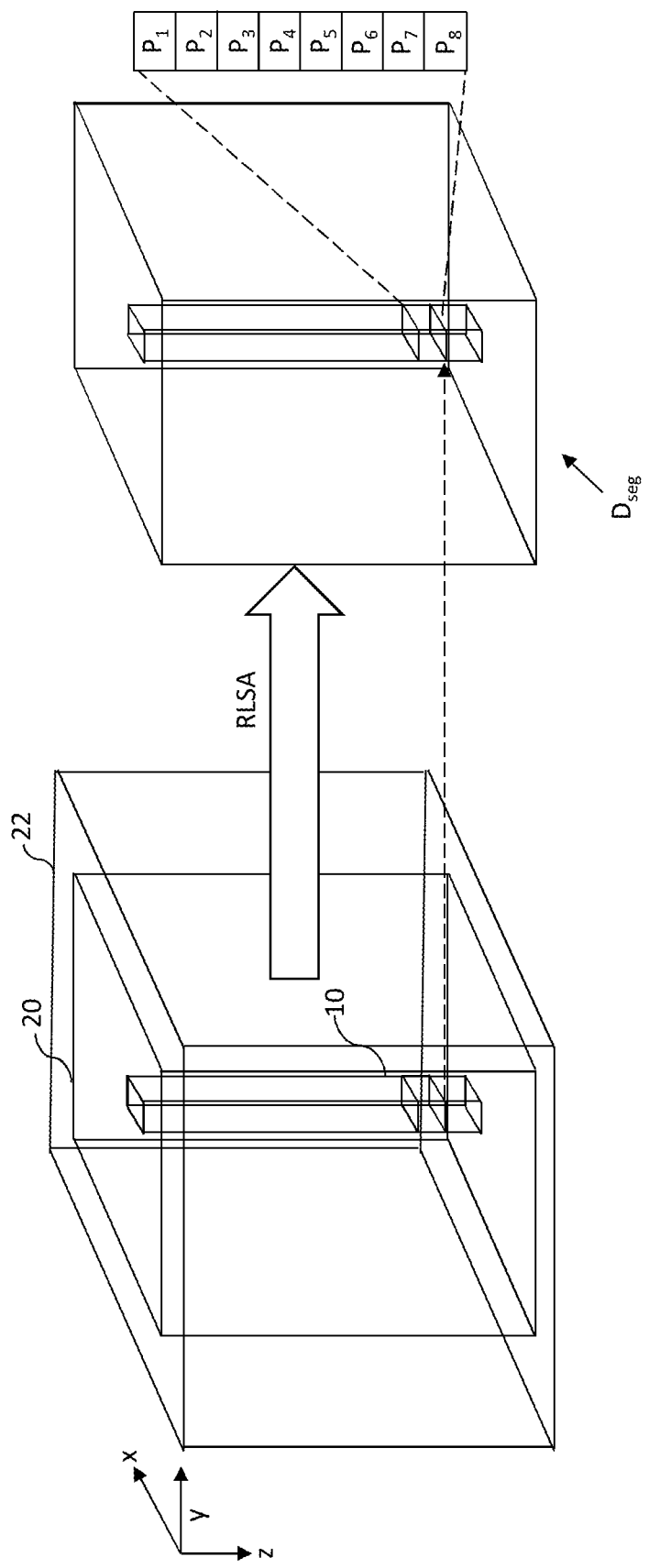
FIG. 3 is a schematic illustration of the generation of a processing of a portion of a C-scan by a retinal layer segmentation algorithm to generate retinal layer segmentation data that is to be provided as an input to the apparatus of the first example embodiment.

By way of example, m=8 in the present example embodiment so that eight probability values, $P_1$ to $P_8$, are generated for the voxel 10, as illustrated in FIG. 3. Each of the probability values $P_1$ to $P_8$ indicates a probability that the voxel 10 belongs to a respective class of a predefined set of eight classes. By way of an example, seven of the eight classes are retinal layer classes associated with respective anatomical layers of the retina (described in more detail below) while the remaining class is a background class associated with a background that does not include any of the seven retinal layers. The predefined set of classes need not, however, include a background class.

Each of the probability values $P_1$ to $P_7$ indicates a probability of the voxel 10 belonging to a respective retinal layer class of a predefined set of retinal layer classes, while probability value $P_8$ indicates a probability of the voxel 10 belonging to the background class. Each retinal layer class of the predefined set is associated with a respective anatomical layer of the retina (or a combination of one or more adjacent anatomical retinal layers). The anatomical layers are anatomically distinct structures of the retina that overlie each other and may be distinguished in the depth axis of an OCT C-scan because of differences in their light diffusive characteristics. Each layer has an inner surface and an outer surface (relative to the vitreous of the eye). The retina can be divided into layers comprising the inner limiting membrane (ILM), the nerve fiber layer (NFL), the ganglion cell layer (GCL), the inner plexiform layer (IPL), the inner nuclear layer (INL), the outer plexiform layer (OPL), the outer nuclear layer (ONL), the outer limiting membrane (OLM), the photoreceptor layer (PL), and the retinal pigmented epithelium (RPE) monolayer.

Although the apparatus 100 of the present example embodiment is arranged to receive and process retinal layer segmentation data $D_{seg}$ generated externally of the apparatus 100, the apparatus of other example embodiments may be arranged to receive an OCT volumetric data of a retinal C-scan and process this data using a retinal layer segmentation algorithm of the kind described above to generate the retinal layer segmentation data $D_{seg}$ itself, before processing the retinal layer segmentation data $D_{seg}$ to generate the segmentation confidence map M as described below.

Referring again to FIG. 2, the apparatus 100 of the present example embodiment comprises a voxel classification module 110, a voxel identification module 120, a confidence evaluation module 130, and a segmentation confidence map generation module 140, whose functionality will be described in more detail below.

Figure 4:
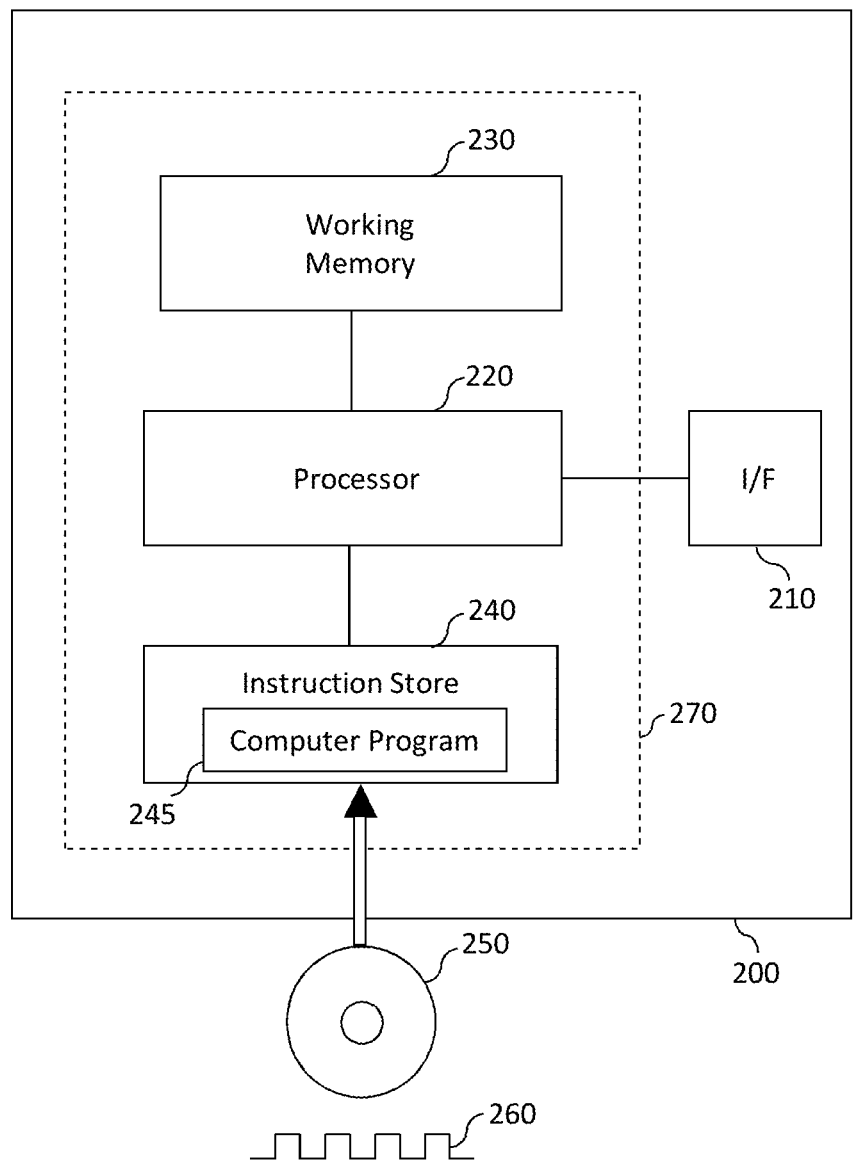
FIG. 4 illustrates an example implementation in programmable signal processing hardware of the first of the example embodiment herein.

FIG. 4 is a schematic illustration of a programmable signal processing hardware 200, which may be configured to perform the operations of the apparatus 100 of the first example embodiment. One or more of the component modules of the apparatus according to any of the other example embodiments described below may also be implemented in the form of a programmable signal processing hardware 200, as illustrated in FIG. 4.

The programmable signal processing apparatus 200 includes a communication interface (I/F) 210, for receiving the retinal layer segmentation data $D_{seg}$ (or the C-scan 22 in case the apparatus 100 is arranged to process the C-scan 22 itself, using the retinal layer segmentation algorithm to generate the retinal layer segmentation data $D_{seg}$) and for outputting the generated segmentation confidence map M, for example to a display for displaying a representation of the segmentation confidence map M, for example in the form of a visual display unit (VDU) such as a computer monitor. The signal processing apparatus 200 further includes a processor (e.g. a Central Processing Unit, CPU) 220, a working memory 230 (e.g. a random access memory) and an instruction store 240 storing a computer program 245 comprising computer-readable instructions which, when executed by the processor 220, cause the processor 220 to perform various functions of the apparatus 100 described herein. The working memory 230 stores information used by the processor 220 during execution of the computer program 245. The instruction store 240 may include a ROM (e.g. in the form of an electrically-erasable programmable read-only memory (EEPROM) or flash memory) which is pre-loaded with the computer-readable instructions. Alternatively, the instruction store 240 may include a RAM or similar type of memory, and the computer-readable instructions of the computer program 245 can be input thereto from a computer program product, such as a non-transitory, computer-readable storage medium 250 in the form of a CD-ROM, DVD-ROM, etc. or a computer-readable signal 260 carrying the computer-readable instructions. In any case, the computer program 245, when executed by the processor 220, causes the processor 220 to execute a method of processing the data received by the communication interface 210 to generate the segmentation confidence map M as described herein. It should be noted, however, that at least some of the components of the apparatus 100 shown in FIG. 2 may alternatively be implemented in non-programmable hardware, such as an application-specific integrated circuit (ASIC).

Figure 2:
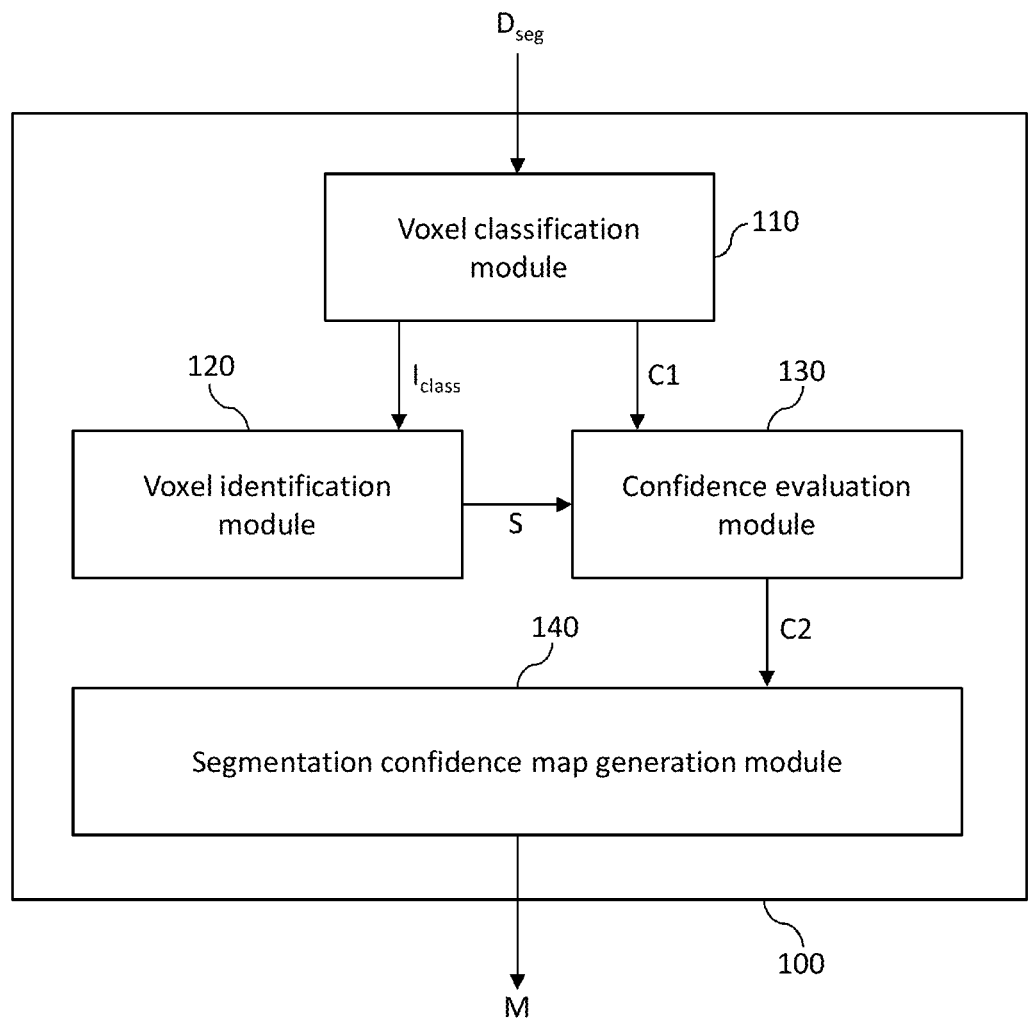
FIG. 2 is a schematic illustration of an apparatus for generating a segmentation confidence map, according to a first example embodiment.
Figure 5:
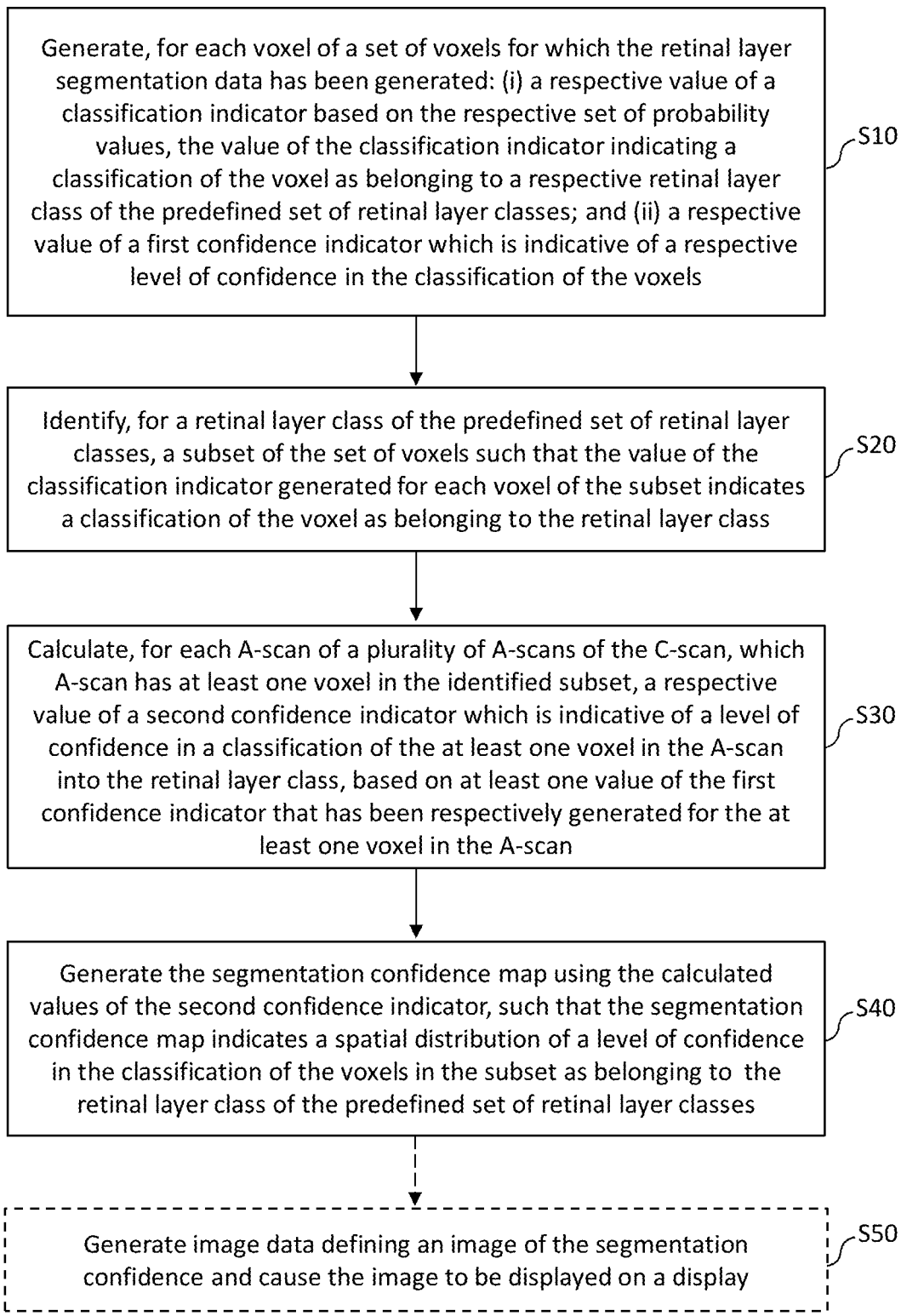
FIG. 5 is a flow diagram illustrating a process by which the apparatus of the first example embodiment generates a segmentation confidence map based on retinal layer segmentation data generated by a retinal layer segmentation algorithm.

FIG. 5 is a flow diagram illustrating a method by which the apparatus 100 of FIG. 2 processes the retinal layer segmentation data $D_{seg}$ to generate the segmentation confidence map M.

In process S10 of FIG. 5, the voxel classification module 110 performs a voxel classification by generating, for each voxel of the set of voxels in the portion 20 of the C-scan 22, for which voxels the retinal layer segmentation data $D_{seg}$ has been generated by the retinal layer segmentation algorithm, a respective value of a classification indicator $I_{class}$ based on the respective set of probability values $P_1$ to $P_8$, the value of the classification indicator $I_{class}$ indicating a classification of the voxel as belonging to a respective class of the set of predefined classes, the respective class being either the background class or one of the retinal layer classes. The voxel classification module 110 may, as in the present example embodiment, perform this voxel classification by classifying the voxel into the class of the predefined set of classes to which the voxel is most likely to belong, as indicated by the highest one of the probability values $P_1$ to $P_8$. The respective value of a classification indicator $I_{class}$ generated for each voxel 10 may be specified as a predefined numerical value associated with the respective class of the predefined set of classes or by a flag value (e.g. 1 or 0) of a flag associated with the respective class of the predefined set of classes, for example. Each group of voxels having a common value of the classification indicator $I_{class}$ defines a respective segmented C-scan.

In addition, in process S10 of FIG. 5, the voxel classification module 110 generates a respective value of the first confidence indicator C1 for each classified voxel 10 in the set of voxels, which value is indicative of a respective level of confidence in the classification of the voxel 10.

The confidence indicator C1 may, as in the present example embodiment, be evaluated for each classified voxel 10 on the basis of the probability values $P_1$ to $P_8$ that have been calculated for the voxel by the retinal layer segmentation algorithm. This confidence indicator evaluation can be done in one of a number of difference ways. For example, in the present example embodiment, the voxel classification module 110 calculates a respective value of the first confidence indicator C1 for each voxel in the portion 20 of the C-scan 22 as a standard deviation of the respective set of probability values $P_1$ to $P_8$. The values of the first confidence indicator C1 thus generated for each voxel of a B-scan in the portion 20 of the C-scan 22 define a (two-dimensional) variability map for the B-scan, which indicates how the level of confidence in the classification of the voxels of the B-scan varies over the B-scan. Since the probability values for each voxel sum to 1, the standard deviation will be higher when one single class has a much larger value than the rest (indicating a high confidence in the classification) and lower when multiple classes have similar values (indicating a low confidence in the classification).

In a variant of the first example embodiment, the voxel classification module 110 may calculate a respective value of the first confidence indicator C1 for each voxel in the portion 20 of the C-scan 22 as 1−D, where D is a difference between a highest probability value in the respective set of probability values and a lowest probability value in the respective set of probability values. Voxels classified with low confidence will have a low value of the difference D (as the probability values in the set will be relatively close to each other), so that 1−D will then be high. B-scan variability maps generated in this way will be similar in appearance to those based on the standard deviation.

In another variant of the example embodiment, the voxel classification module 110 may calculate a respective value of the first confidence indicator C1 for each voxel in the portion 20 of the C-scan 22 as 1−P, where P is a difference between a highest probability value in the respective set of probability values and a second highest probability value in the respective set of probability values. Voxels classified with low confidence will have a low value of the difference P, and 1−P will be therefore high, similar to the variant noted above.

Although the confidence indicator C1 is evaluated for each classified voxel 10 on the basis of the probability values $P_1$ to $P_8$ that have been calculated for the voxel by the retinal layer segmentation algorithm in the present example embodiment, the confidence indicator C1 may be evaluated for each classified voxel 10 in other ways in alternative example embodiments, independently of the probability values generated by the retinal layer segmentation algorithm. For example, in an alternative embodiment, the voxel classification module 110 may generate a respective value of the first confidence indicator C1 for each voxel in the set using a value of a local image quality metric that indicates an image quality of a region of an image that has been rendered from a part of the C-scan 22 containing the voxel 10. The local image quality metric may take one of many different forms, for example: a local Signal-to-Noise Ratio (SNR) of a small B-scan patch centred on the voxel; a comparative measure (e.g., a ratio or a difference) of the voxel intensity with respect to neighbouring voxels or the rest of the voxels in the B-scan;

or a comparative measure (e.g., a ratio or a difference) of the average intensity of an entire A-scan with respect to neighbouring A-scans or the rest of the voxels in the B-scan. In the latter example, all voxels in the A-scan would have the same level of confidence.

As a further alternative, the voxel classification module 110 may generate a respective value of the first confidence indicator C1 for each voxel in the set based on post-processing checks to verify the presence of outliers in the segmentation output. Image processing techniques (e.g. filtering, thresholding, and morphological operations) applied to the B-scan images or to segmentation confidence maps, or to their en-face projections or to retinal layer thickness maps, can help identify the following in post-processing:
1. A-scans where the OCT scan pattern is occluded by imaging artefacts, floaters in the vitreous, or shadow effects of retinal blood vessels.
2. A-scans where non-contiguous voxels have been identified as belonging to the same class (this could be an indication of pathology or low image quality).
3. A-scans where the segmentation output does not respect the physiological depth order of retinal layers (e.g. a cluster of voxels labelled as nerve fiber layer identified underneath a cluster of voxels labelled as photoreceptors.
4. A-scans where one layer presents a thickness discontinuity (i.e. many more or many fewer voxels have been labelled as belonging to a certain class) with respect to the neighbouring A-scans.

Segmentation confidence maps can then be created by assigning a low (or zero) confidence to the areas listed above.

In process S20 of FIG. 5, the voxel identification module 120 identifies, for a retinal layer class of interest from among the predefined set of retinal layer classes, a subset S of the set of voxels such that the value of the classification indicator $I_{class}$ generated for each voxel of the subset S indicates a classification of the voxel as belonging to the retinal layer class. In this way, the voxel identification module 120 picks out, from among the set of voxels for which the probability values have been calculated, a subset of the voxels which have been classified in process S10 of FIG. 5 as belonging to one of the retinal layer classes of the predefined set of retinal layer classes. The retinal class of interest may be selectable by a user using an input device (such as a computer mouse, keyboard, trackpad or the like) connected to the apparatus 100, for example via the I/F module 210 where the apparatus 100 is implemented in the form of a programmable signal processing apparatus 200 as shown in FIG. 4.

In process S20 of FIG. 5, the voxel identification module 120 may additionally or alternatively identify, for the background class, a subset S of the set of voxels such that the value of the classification indicator $I_{class}$ generated for each voxel of the subset S indicates a classification of the voxel as belonging to the background class. Although process S20 is shown to follow process S10 in FIG. 5, it should be noted that process S20 may run concurrently with process S10, with the voxel identification module 120 performing the identification described above using values of the classification indicator $I_{class}$ as they are generated by the voxel identification module 110.

In process S30 of FIG. 5, the confidence evaluation module 130 calculates, for each A-scan of a plurality of A-scans of the C-scan 22, which A-scan has at least one voxel 10 in the identified subset S, a respective value of a second confidence indicator C2 which is indicative of a level of confidence in a classification of the at least one voxel in the A-scan into the retinal layer class, based on at least one value of the first confidence indicator C1 that has been respectively generated for the at least one voxel in the A-scan. In other words, the value of the second confidence indicator C2 is calculated for each A-scan having one or more voxels classified as belonging to the retinal layer class of interest using the value(s) of the first confidence indicator C1 which has/have been calculated in process S10 for each of the aforementioned one or voxels in the A-scan. The value of the second confidence indicator C2 is calculated for each A-scan having one or more voxels classified as belonging to the retinal layer class of interest by calculating an average (e.g. a median, a mean or a refined mean based on values that remain after eliminating outliers) of the values of the first confidence indicator C1 which have been calculated in process S10 for each of the aforementioned one or voxels in the A-scan. Put another way, for the retinal layer class of interest, values in the variability maps mentioned above, which are labelled as belonging to the retinal layer class of interest according to the segmented C-scan, are averaged in the z-axis (depth direction).

In process S40 of FIG. 5, the segmentation confidence map generation module 140 generates the segmentation confidence map M using the values of the second confidence indicator C2 calculated in process S30 of FIG. 5, such that the segmentation confidence map M indicates a spatial distribution of a level of confidence in the classification of the voxels in the subset S into the retinal layer class of interest. The segmentation confidence map generation module 140 may, as in the present example embodiment, generate the segmentation confidence map M by assigning, to each data element in a two-dimensional array of data elements defining the segmentation confidence map M, which data elements are associated with corresponding A-scans in the portion 20 of the C-scan 22 (i.e. an A-scan which is correspondingly located in the x-y plane of the C-scan 22 as the data element in the two-dimensional data element array of the segmentation confidence map M), a respective value which indicates the value of the second confidence indicator C2 calculated for the A-scan that corresponds to the data element. The segmentation confidence map generation module 140 may then normalize the segmentation confidence map M, and fill any empty location in the two-dimensional array of the map M (corresponding to an A-scan in the C-scan 22 which contained no voxel classified as belong to the retinal layer class of interest) with the lowest value of the calculated values of the second confidence indicator C2.

In optional process S50 in FIG. 5, the segmentation confidence map generation module 140 generates image data defining an image of at least a portion of the (optionally normalised) segmentation confidence map M, and may furthermore cause the image to be displayed on the aforementioned display. The segmentation confidence map generation module 140 may additionally display a single overall confidence score calculated as an average of the values of the second confidence indicator C2 in the segmentation confidence map M, and/or local confidence scores calculated as respective averages of the values of the second confidence indicator C2 in predefined sectors of the segmentation confidence map M. The segmentation confidence map generation module 140 may cause the image defined by the image data to be displayed on the display in a variety of different forms, to provide visual interpretability to the results of the retinal layer segmentation.

For example, the image may, as in the present example embodiment, be displayed as an overlay on an OCT en-face image shown on the display, the en-face image being based on the subset of voxels from the C-scan 22 that have been classified as belonging to the retinal layer class of interest. This overlay may allow the user to easily identify any region of the en-face image where the retinal layer segmentation has not been performed to a high level of confidence, for example.

In another example embodiment, the image may be displayed as an overlay on a retinal layer thickness map which is displayed on the display, wherein the retinal layer thickness map is based on the subset of voxels of the C-scan that have been classified as belonging to the retinal layer class of interest and indicates how the determined thickness of this layer varies (laterally) across the retina. This overlay may allow the user to easily identify any region of the thickness map in which the retinal layer thickness has not been determined reliably, for example.

In a further example embodiment, the image may be of a one-dimensional section of the confidence map M, which is displayed in the form of a plot aligned with a representation of a B-scan displayed on the display, wherein the B-scan comprises voxels which have been classified as belonging to the retinal layer class of interest and are from A-scans whose associated values of the second confidence indicator C2 have been used to generate the one-dimensional section of the confidence map M. The plot may be overlaid on or displayed alongside the representation of the B-scan on the display, with the alignment allowing the user to identify any part of the displayed representation of the B-scan which contains an unreliable segmentation of the retinal layer.

The segmentation confidence map M generated by the segmentation confidence map generation module 140 can be used not only to aid interpretation of retinal layer segmentation results but also to produce more reliable calculations of retinal layer thickness measures (as described in the third and fourth example embodiments below), to compute metrics for logging OCT layer segmentation confidence, or to create alerts for the user about possibly challenging areas in an OCT volumes (e.g., low quality, imaging artefacts, lesions, other indefinite structures), for example.

It should also be noted that the first example embodiment is not limited to generating a single segmentation confidence map for a single retinal layer class of the predefined set of classes but may additionally generate a respective segmentation confidence map for each of one or more of the remaining classes, including the background class. A segmentation confidence map generated for the background class may be used to identify a floater or some other structure outside the retina as a likely cause of a feature in an en-face OCT image of the retina or a fundus image registered to the segmentation confidence map, for example.

The segmentation confidence map generation module 140 may be arranged to determine whether the segmentation confidence map M indicates a level of confidence in the classification of the voxels in the subset S as belonging to the retinal layer class that is below a confidence threshold value and, in a case where the segmentation confidence map M is determined to indicate a level of confidence in the classification of the voxels that is below the confidence threshold value, generate an alert (e.g. in the form of a message or other indication displayed on the display, and/or an audio signal) to alter a user to this result of the determination. For example, where the segmentation confidence map generation module 140 generates image data defining an image of at least a portion of the segmentation confidence map M, the alert may be provided by a part of the image of the segmentation confidence map M, wherein the level of confidence in the classification of the voxels in the subset S as belonging to the retinal layer class is below the confidence threshold value, being highlighted on the display, for example by being show in a predetermined color (e.g. red) and/or by flashing (i.e. being repeatedly displayed and withdrawn from display).

Second Example Embodiment

Figure 6:
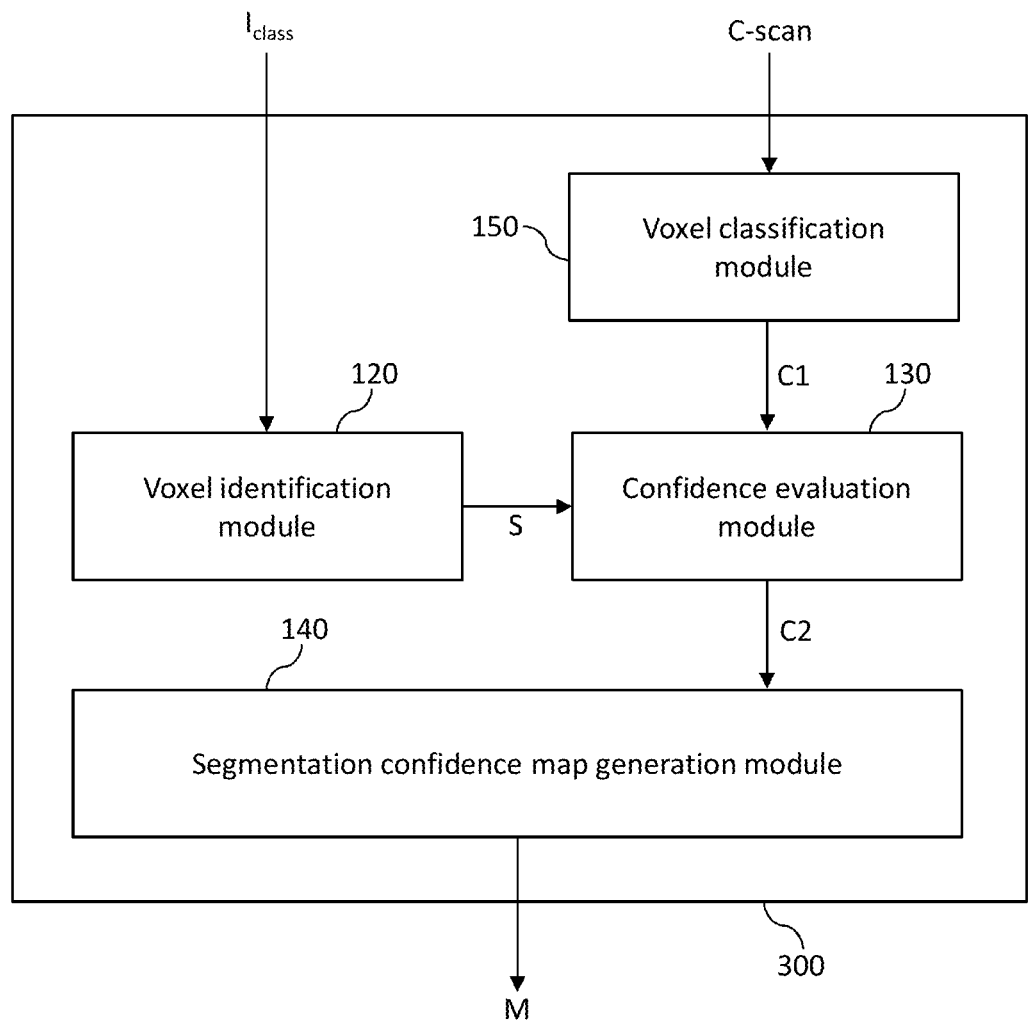
FIG. 6 is a schematic illustration of an apparatus for generating a segmentation confidence map, according to a second example embodiment.

FIG. 6 is a schematic illustration of an apparatus 300 for generating a segmentation confidence map M according to a second example embodiment. The apparatus 300 differs from the apparatus 100 of the first example embodiment by having a confidence indicator evaluation module 150 in place of the voxel classification module 110, by the voxel identification module 120 being arranged to receive values of the classification indicator $I_{class}$ that have been generated by a retinal layer segmentation algorithm, and by the confidence evaluation module 130 being arranged to receive values of the first confidence indicator C1 that have been generated by the confidence indicator evaluation module 150. The apparatus 300 is the same as the apparatus 100 of the first example embodiment in all other respects. The following description of the second example embodiment will therefore focus on the aforementioned differences.

Figure 7:
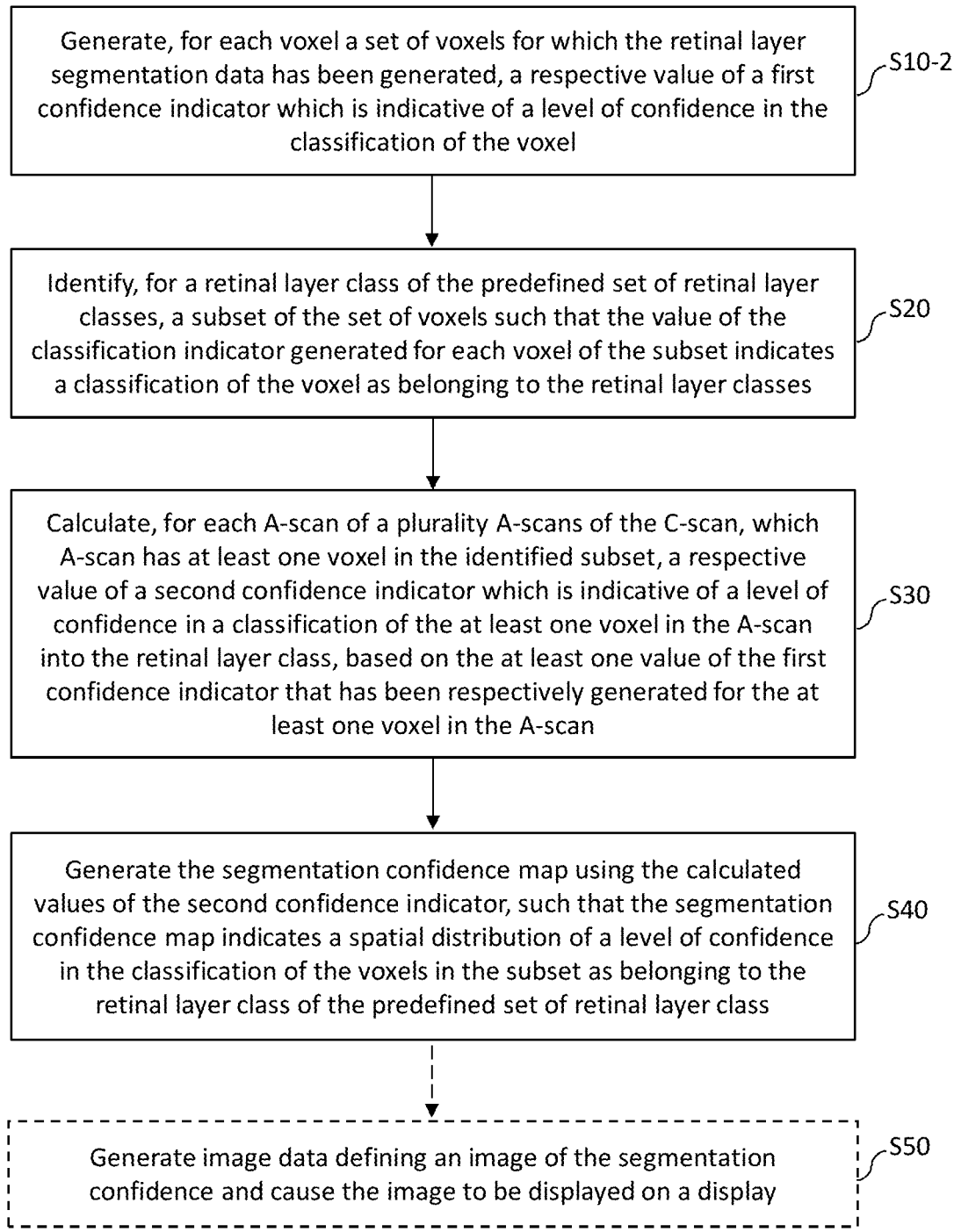
FIG. 7 is a flow diagram illustrating a process by which the apparatus of the second example embodiment generates a segmentation confidence map based on retinal layer segmentation data generated by a retinal layer segmentation algorithm.

FIG. 7 is a flow diagram illustrating a method by which the apparatus 300 of FIG. 6 processes a part or whole of a C-scan of a retina, and values of a classification indicator $I_{class}$ that have been generated by a retinal layer segmentation algorithm processing the part or while of the C-scan, to generate a segmentation confidence map M of the form described above. The retinal layer segmentation algorithm used to generate the values of the classification indicator $I_{class}$ input to the apparatus 300 may be any type of segmentation algorithm known to those skilled in the art that is capable of generating classification indicator values of the kind described above, and need not be probabilistic in nature, as in the case of the first example embodiment (where the RLSA returns a set of probability values for each voxel, rather than a single segmentation/classification result). In the present example embodiment, the retinal layer segmentation algorithm generates, for each voxel of at least a portion of a C-scan of a retina, a respective value of a classification indicator $I_{class}$ indicating a classification of the voxel as belonging to a retinal layer class of the predefined set of retinal layer classes.

In process S10-2 of FIG. 7, the confidence indicator evaluation module 150 generates, for each voxel of a set of voxels for which the retinal layer segmentation data has been generated, a respective value of a first confidence indicator C1 which is indicative of a level of confidence in the classification of the voxel 10. The confidence indicator evaluation module 150 may, as in the present example embodiment, generate a respective value of the first confidence indicator C1 for each voxel in the set using a value of a local image quality metric that indicates an image quality of a region of an image that has been rendered from a part of the C-scan 22 containing the voxel 10. As a further alternative, the confidence indicator evaluation module 150 may generate a respective value of the first confidence indicator C1 for each voxel in the set based on post-processing checks to verify the presence of outliers in the segmentation output.

In process S20 of FIG. 7, the voxel identification module 120 identifies, for a retinal layer class of the predefined set of retinal layer classes, a subset S of the set of voxels such that the value of the classification indicator $I_{class}$ generated by the segmentation algorithm for each voxel of the subset S indicates a classification of the voxel as belonging to the retinal layer class.

In process S30 of FIG. 7, the confidence evaluation module 130 calculates, for each A-scan of a plurality of A-scans of the C-scan, which A-scan has at least one voxel in the identified subset S identified by the voxel identification module 120, a respective value of a second confidence indicator C2 which is indicative of a level of confidence in a classification of the at least one voxel in the A-scan into the retinal layer class, based on at least one value of the first confidence indicator C1 that has been respectively generated by the confidence indicator evaluation module 130 for the at least one voxel in the A-scan.

Processes S40 and S50 in FIG. 7 are the same as the identically labelled processes in FIG. 5, which have been described in detail above.

Third Example Embodiment

Figure 8:
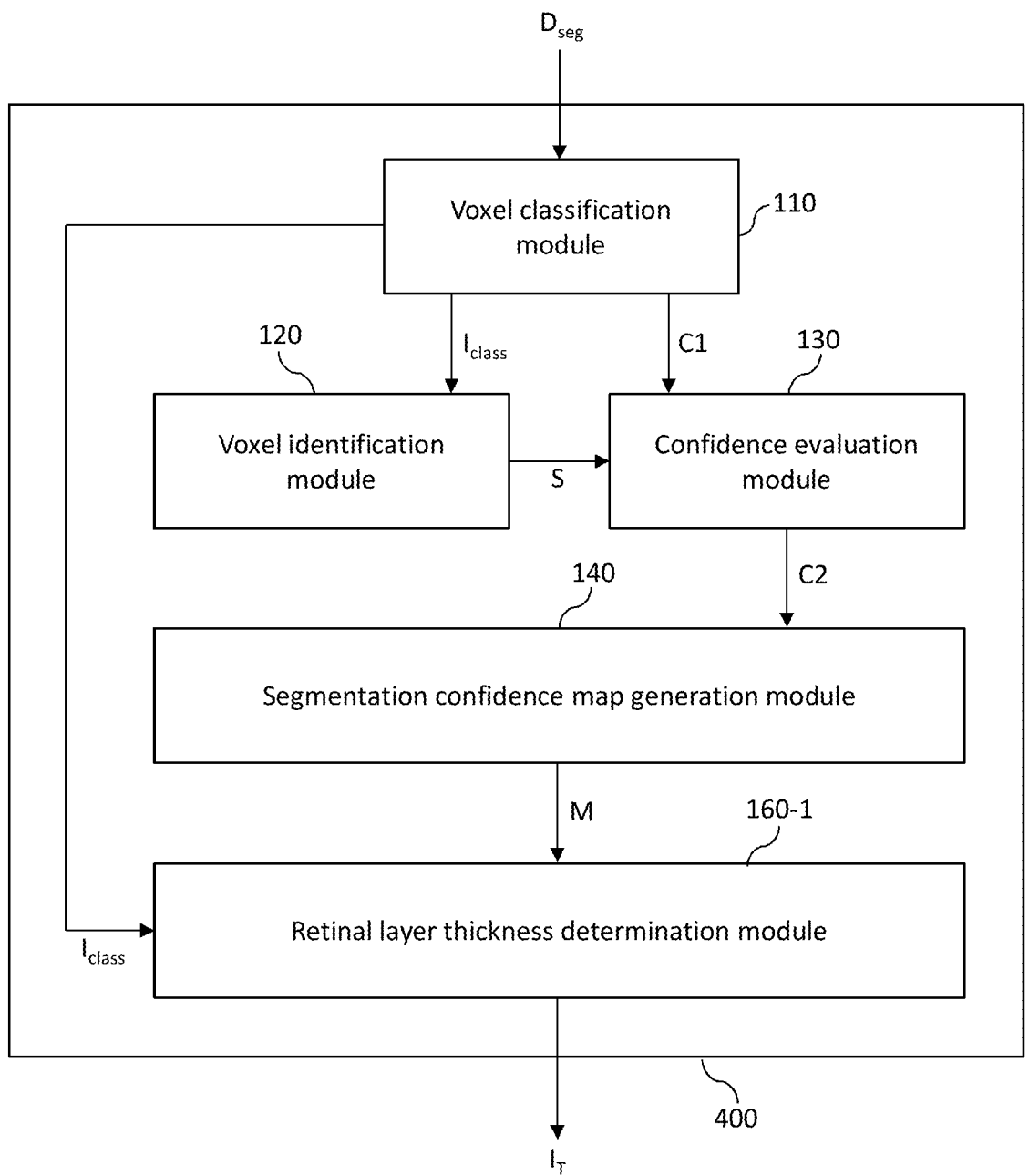
FIG. 8 is a schematic illustration of an apparatus for generating a segmentation confidence map according to a third example embodiment.

FIG. 8 is a schematic illustration of an apparatus 400 for generating a segmentation confidence map M according to a third example embodiment. The apparatus 400 differs from the apparatus 100 of the first example embodiment by further comprising a retinal layer thickness determination module 160-1, which is arranged to use the segmentation confidence map M generated by the segmentation confidence map generation module 140 and values of the classification indicator $I_{class}$ generated by the voxel classification module 110 to determine an indication $I_T$ of a thickness of a layer of the retina that is associated with the retinal layer class of interest. In all other respects, the apparatus 400 is the same as the apparatus 100 of the first example embodiment. The operation of the retinal layer thickness determination module 160-1 will now be described with reference to FIG. 9.

Figure 9:
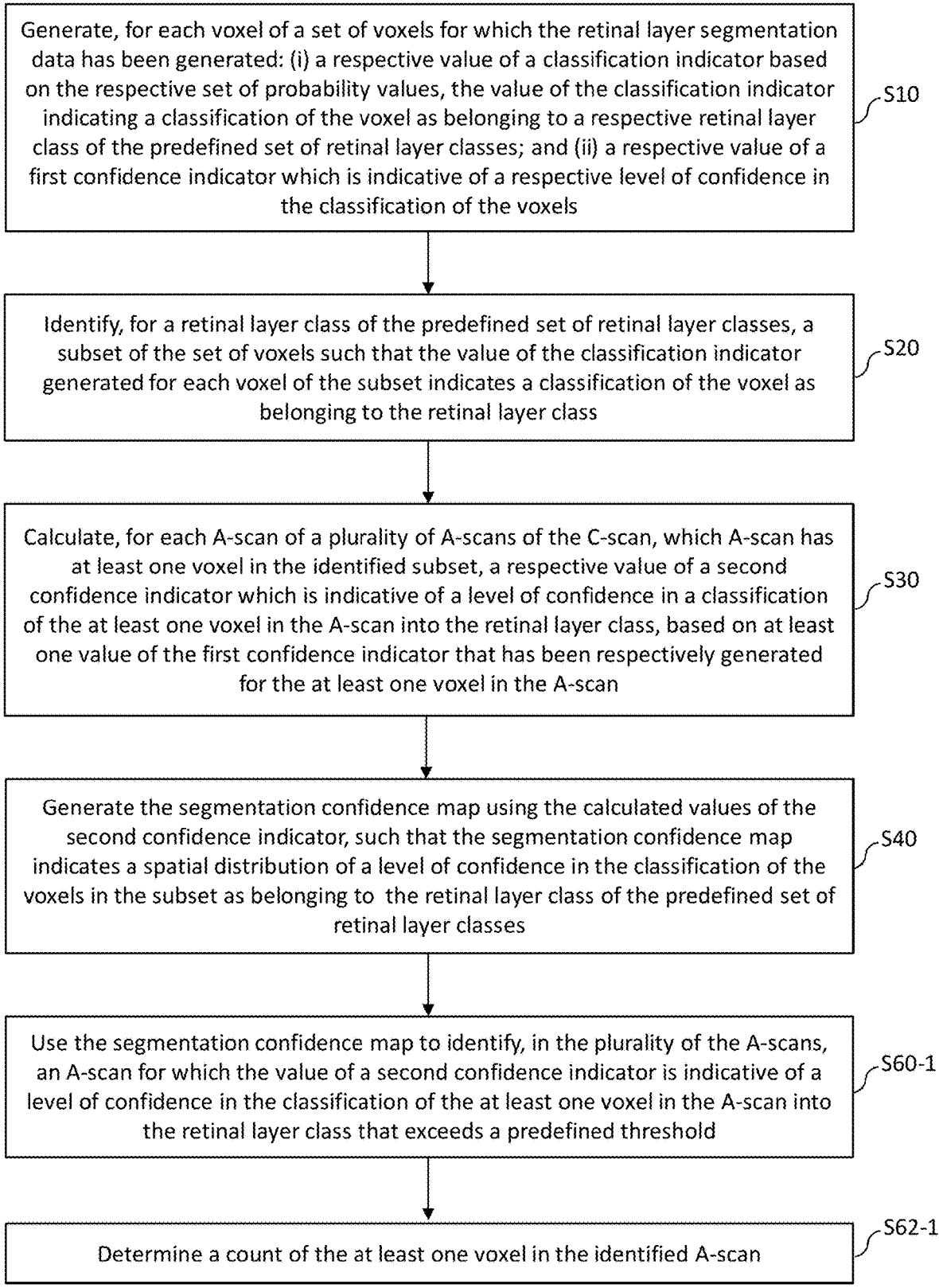
FIG. 9 is a flow diagram illustrating a process by which the apparatus of the third example embodiment generates a segmentation confidence map and uses the segmentation confidence map to determine an indication of a retinal layer thickness.

FIG. 9 is a flow diagram illustrating a process by which the apparatus 400 of the present example embodiment generates a segmentation confidence map and uses the segmentation confidence map to determine the indication $I_T$ of the thickness of the layer of the retina.

Processes S10 to S40 as the same as those described above with reference to FIG. 5.

In process S60-1 of FIG. 9, the retinal layer thickness determination module 160-1 uses the generated segmentation confidence map M to identify, in the plurality of A-scans, an A-scan for which the associated value of a second confidence indicator C2 is indicative of a level of confidence in the classification of the at least one voxel in the A-scan into the retinal layer class that exceeds a predefined threshold. An A-scan in which a group of one or more voxels have been classified into the retinal layer class of interest with a sufficiently high degree of confidence, and which can therefore be used to obtain a reliable estimate of the thickness of the associated retinal layer, is thus identified in process S60-1 of FIG. 9.

In process S60-1 of FIG. 9, the retinal layer thickness determination module 160-1 may, as in the present example embodiment, binarize the segmentation confidence map M generated for the retinal layer segmentation class of interest in process S40 of FIG. 9 according to a threshold value t, so that data elements in the two-dimensional data element array defining the segmentation confidence map M having values greater than t are each set to contain a value of "1", while the remaining data elements are each set to contain a value of "0", for example. The binarized segmentation confidence map can be used to highlight locations of A-scans in the C-scan 22 for which a reliable evaluation of retinal layer thickness can be made. The A-scan identified in process S60-1 of FIG. 9 may be any A-scan which is at location in the x-y plane of the C-scan 22 which corresponds to a location in the binarized segmentation confidence map of a data element containing the value of "1" in this example.

In process S62-1 of FIG. 9, the retinal layer thickness determination module 160-1 determines, as the indication $I_T$ of the thickness of the layer of the retina, a count of the at least one voxel (for which the voxel classification module 110 has generated a value of the classification indicator $I_{class}$ which indicates a classification of the voxel(s) as belonging to the retinal layer class of interest) of the A-scan identified in process S60-1 of FIG. 9. The one or more voxels in the identified A-scan that are to be counted may, as in the present example embodiment, be identified by looking up the values of the classification indicator $I_{class}$ generated for the A-scan by the voxel classification module 110, or alternatively by identifying one or more voxels in the A-scan that belong to the subset S of voxels that have been identified by the voxel identification module 120 as belonging to the retinal layer class of interest.

Although the result of process S62-1 of FIG. 9 may provide a sufficient indication of the thickness of the retinal layer, the retinal layer thickness determination module 160-1 may, as in the present example embodiment, repeat processes S60-1 and S62-1 to identify, using the segmentation confidence map M, a second plurality of A-scans in the plurality of A-scans, wherein the respective value of a second confidence indicator C2 calculated for each A-scan of the second plurality of A-scans is indicative of a respective level of confidence in the classification of the at least one voxel in the A-scan into the retinal layer class of interest that exceeds the predefined threshold. In repeating processes S60-1 and S62-1, the retinal layer thickness determination module 160-1 determines, for each A-scan of the identified second plurality of A-scans, a respective count of the at least one voxel in the A-scan, as described above.

The retinal layer thickness determination module 160-1 may calculate the average of these counts to obtain a reliable measure of the thickness of the retinal layer of interest in the region of the retina covered by the portion 20 of the C-scan 22, using only high-confidence segmentation data. Additionally or alternatively, the retinal layer thickness determination module 160-1 may, as in the present example embodiment, determine a respective indication of the thickness of the layer of the retina for each predefined region of a plurality of predefined regions of the retina that are covered by the portion 22 of the C-scan 22, from which predefined region a respective set of A-scans of the identified second plurality of A-scans has been acquired, by calculating an average of the counts determined for the A-scans of the set of A-scans.

The number of the predefined regions is not limited, and their arrangement on the retina may take various different forms. For example, the predefined regions of the retina may, as in the present example embodiment, be the nine regions of an Early Treatment Diabetic Retinopathy Study (ETDRS) grid. The indications of retinal layer thickness thus determined by the retinal layer thickness determination module 160-1 may be scaled to values of thickness expressed in length measurement units such as microns or the like, and may be indicated in any desired form in the respective regions of an ETDRS grid that is displayed on the above-mentioned display, for example as numerical values or by color coding.

The retinal layer thickness determination module 160-1 may record, for each ETDRS region, a fraction of the A-scans acquired in the region that are not among the identified second plurality of A-scans. The fraction recorded for each ETDRS grid region may be compared with a threshold value tr. Where the fraction exceeds the threshold tr, the thickness value calculated for the region may be highlighted as unreliable or not shown on the display, otherwise the thickness value calculated for the region may be indicated on the displayed ETDRS grid as described above. A respective confidence score may be derived from each fraction and displayed on the display so as to provide an indication of the reliability of the average retinal layer thickness in the corresponding ETDRS grid region (where indicated).

Although processing operations performed by the apparatus 400 of the present example embodiment to determine an indication $I_T$ of the thickness of a single layer of the retina that is associated with the retinal layer class of interest have been described above, similar operations may additionally be performed to determine a respective indication of the thickness one or more other layers of the retina that is/are associated with the corresponding one or more retinal layer classes of the predefined set of classes.

In a variant of the third example embodiment, the retinal layer thickness determination module 160-1 may, following a binarization of the segmentation confidence map M as described above, count, in each A-scan in the portion 20 of the C-scan 22, the respective number of voxels for which the voxel classification module 110 has generated a value of the classification indicator $I_{class}$ which indicates a classification of the voxels as belonging to the retinal layer class of interest. The result is a 'thickness map' that indicates a distribution of the voxel count values across the array of A-scans. The retinal layer thickness determination module 160-1 may then mask the thickness map using the binarized segmentation confidence map and discard voxel count values obtained from A-scans that are located at locations in the array of A-scans that correspond to locations of data elements in the normalized segmentation confidence map having a data element value of "0". Accordingly, the apparatus of this variant may (similar to the third example embodiment) calculate retinal layer thickness values that are more reliable than those calculated by some conventional techniques, which may be skewed by low-confidence segmentation results caused by imaging (or other) artefacts on the OCT volumetric data, for example.

The apparatus 400 of the third example embodiment or any of its variants may be modified by providing the retinal layer thickness determination module 160-1 in combination with the apparatus 300 of the second example embodiment (instead of the apparatus 100 of the first example embodiment), so that the retinal layer thickness determination module 160-1 is provided with the segmentation confidence map M generated by the segmentation confidence map generation module 140 and values of the classification indicator $I_{class}$ generated by the voxel classification module 110 of the second example embodiment.

Fourth Example Embodiment

Figure 10:
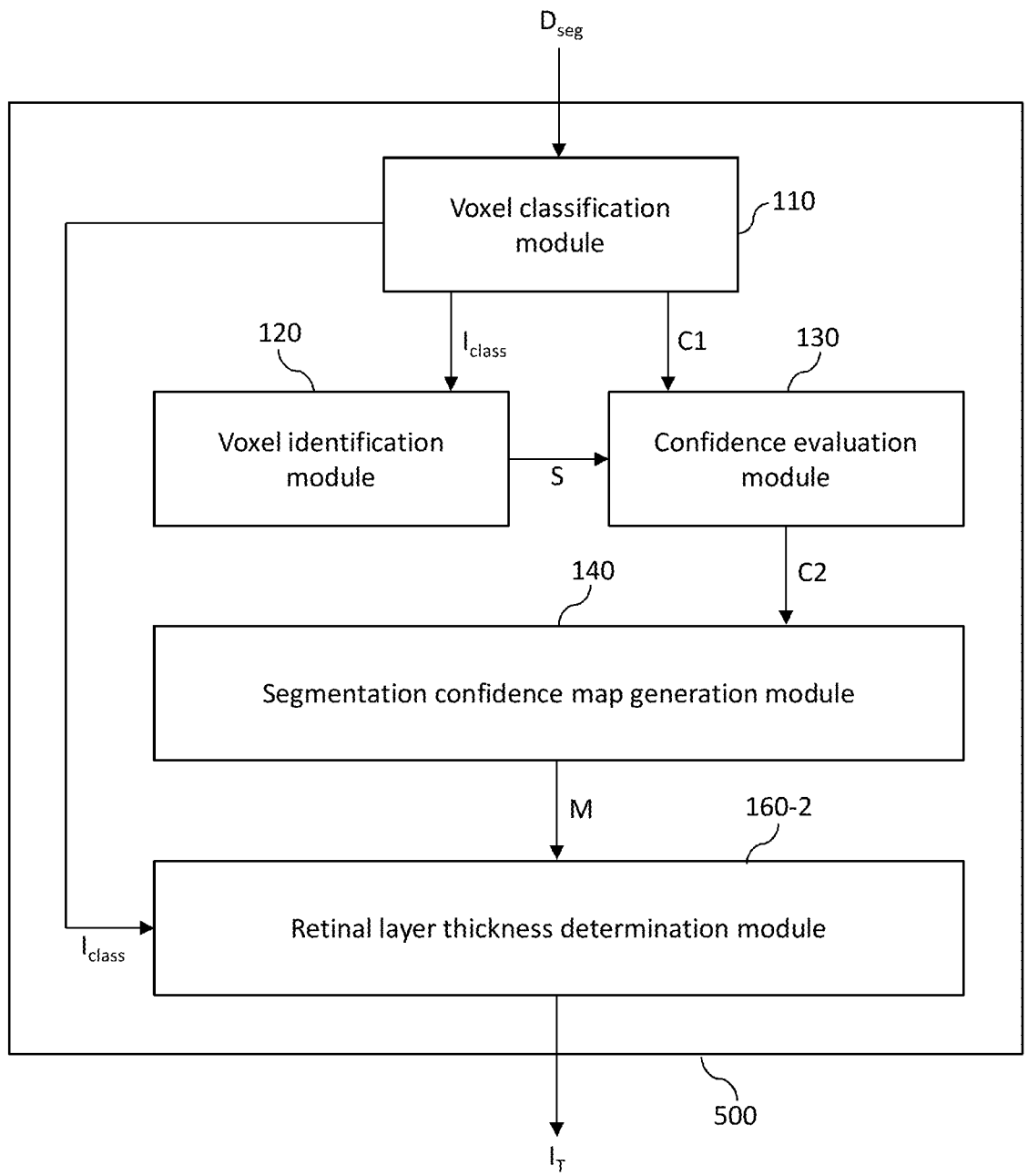
FIG. 10 is a schematic illustration of an apparatus for generating a segmentation confidence map according to a fourth example embodiment.

FIG. 10 is a schematic illustration of an apparatus 500 for generating a segmentation confidence map M according to a fourth example embodiment. The apparatus 500 differs from the apparatus 100 of the first example embodiment by further comprising a retinal layer thickness determination module 160-2, which is arranged to use the segmentation confidence map M generated by the segmentation confidence map generation module 140 and values of the classification indicator $I_{class}$ generated by the voxel classification module 110 to determine an indication $I_T$ of a thickness of a layer of the retina that is associated with the retinal layer class of interest. In all other respects, the apparatus 500 is the same as the apparatus 100 of the first example embodiment. The operation of the retinal layer thickness determination module 160-2 will now be described with reference to FIG. 11. The retinal layer thickness determination module 160-2 is a variant of the retinal layer thickness determination module 160-1 of the third example that determines the indication $I_T$ of the retinal layer thickness in an alternative way, as described below.

Figure 11:
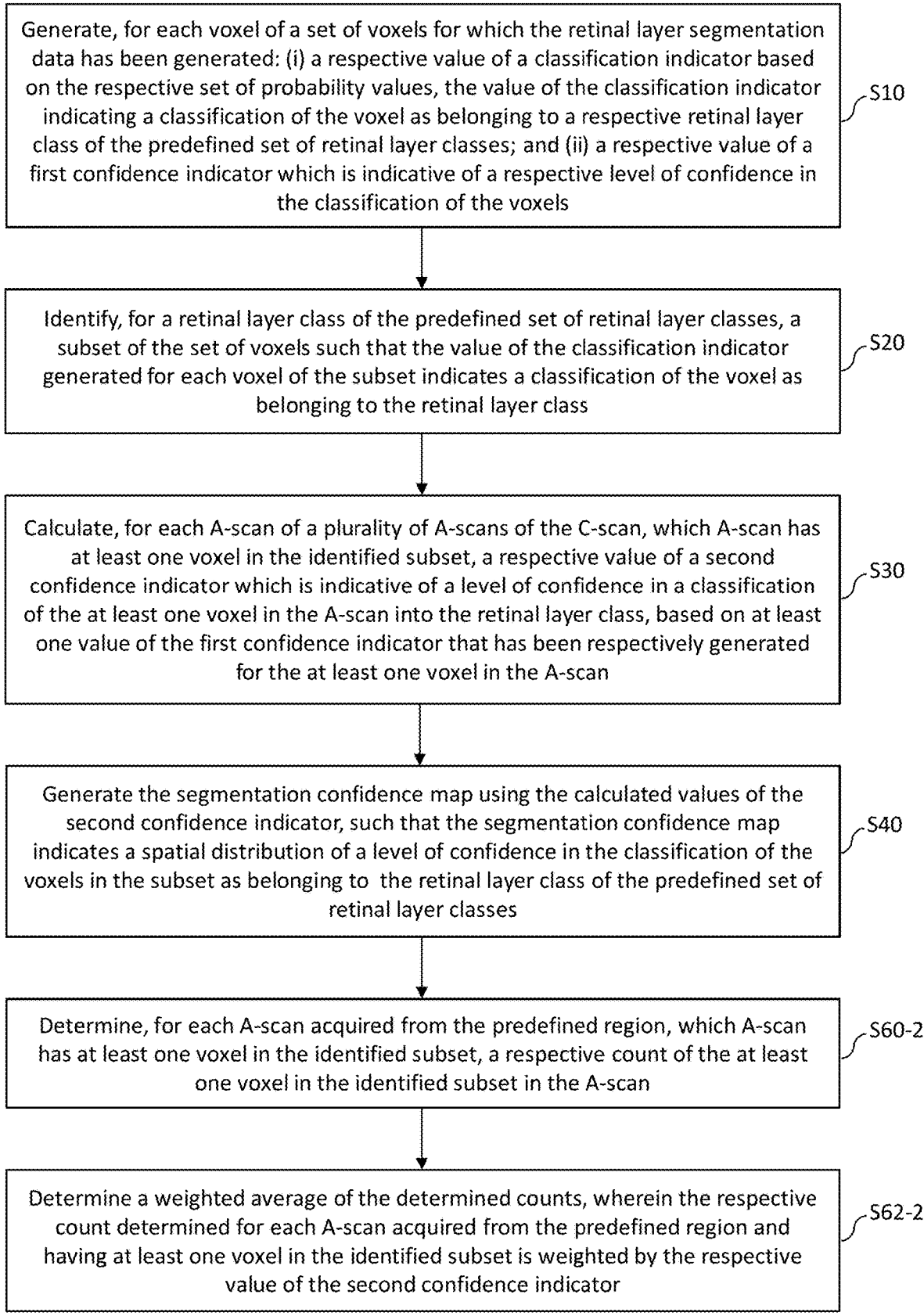
FIG. 11 is a flow diagram illustrating a process by which the apparatus of the fourth example embodiment generates a segmentation confidence map and uses the segmentation confidence map to determine an indication of a retinal layer thickness.

FIG. 11 is a flow diagram illustrating a process by which the apparatus 500 of the present example embodiment generates a segmentation confidence map and uses the segmentation confidence map to determine the indication $I_T$ of the thickness of the layer of the retina.

Processes S10 to S40 as the same as those described above with reference to FIG. 5.

In process S60-2 of FIG. 11, the retinal layer thickness determination module 160-2 determines, for each A-scan of a group of A-scans having one or more voxels 10 for which the voxel classification module 110 has generated a value of the classification indicator $I_{class}$ which indicates a classification of the voxel(s) as belonging to the retinal layer class of interest, a respective count of one or more voxels. The voxel(s) to be counted may, as in the present example embodiment, be identified by looking up the values of the classification indicator $I_{class}$ generated for the A-scan by the voxel classification module 110, or alternatively by identifying one or more voxels in the A-scan that belong to the subset S of voxels that have been identified by the voxel identification module 120 as belonging to the retinal layer class of interest.

In process S62-2 of FIG. 11, the retinal layer thickness determination module 160-2 calculates, a weighted average of the counts determined in process S60-2 of FIG. 11, wherein the respective count determined for each A-scan having at least one voxel 10 in the identified subset S is weighted by the respective value of the second confidence indicator C2 that has been calculated by the confidence evaluation module 130 and is included in the segmentation confidence map M.

The weighted average may thus be calculated for all the A-scans in the subset S, which have one or more voxels 10 for which the voxel classification module 110 has generated a value of the classification indicator $I_{class}$ indicating a classification of the voxel(s) as belonging to the retinal layer class of interest. In this case, the weighted average can provide a reliable measure of the thickness of the retinal layer of interest in the region of the retina covered by the portion 20 of the C-scan 22, as A-scans that have been segmented with high confidence are given more weight (and thus provide a greater contribution to the weighted average) than A-scans that have been segmented with low confidence.

The retinal layer thickness determination module 160-2 may, as in the present example embodiment, determine a respective indication of the thickness of the layer of the retina in this way for each predefined region of a plurality of predefined regions of the retina that are covered by the portion 22 of the C-scan 22, from which predefined region a respective set of A-scans of the identified second plurality of A-scans has been acquired, by calculating a weighted average of the counts determined for the A-scans of the set of A-scans.

The number of the predefined regions is not limited, and their arrangement on the retina may take various different forms. For example, the predefined regions of the retina may, as in the present example embodiment, be the nine regions of an ETDRS grid. The indications of retinal layer thickness thus determined by the retinal layer thickness determination module 160-2 may be scaled to values of thickness expressed in length measurement units such as microns or the like, and may be indicated in any desired form in the respective regions of an ETDRS grid that is displayed on the above-mentioned display, for example as numerical values or by color coding.

The retinal layer thickness determination module 160-2 may record, for each ETDRS region, a confidence level for the weighted average calculated for the region, based on values of the second confidence indicator C2 that were used in the weighting. The confidence level recorded for each ETDRS grid region may be compared with a threshold value tr'. Where the confidence level exceeds the threshold tr', the thickness value calculated for the region may be highlighted as unreliable or not shown on the display, otherwise the thickness value calculated for the region may be indicated on the displayed ETDRS grid as described above. The confidence level recorded for an ETDRS grid region, or a confidence score derived from the confidence level, may be displayed on the display so as to provide an indication of the reliability of the average retinal layer thickness in the ETDRS grid region (where indicated).

Although processing operations performed by the apparatus 500 of the present example embodiment to determine an indication $I_T$ of the thickness of a single layer of the retina that is associated with the retinal layer class of interest have been described above, similar operations may additionally be performed to determine a respective indication of the thickness one or more other layers of the retina that is/are associated with the corresponding one or more retinal layer classes of the predefined set of classes.

The apparatus 500 of the fourth example embodiment or any of its variants may be modified by providing the retinal layer thickness determination module 160-2 in combination with the apparatus 300 of the second example embodiment (instead of the apparatus 100 of the first example embodiment), so that the retinal layer thickness determination module 160-2 is provided with the segmentation confidence map M generated by the segmentation confidence map generation module 140 and values of the classification indicator $I_{class}$ generated by the voxel classification module 110 of the second example embodiment.

Although the retinal layer thickness determination module 160-1 of the third example embodiment and the retinal layer thickness determination module 160-2 of the fourth example embodiment are both arranged to use the segmentation confidence map M generated by the segmentation confidence map generation module 140 to determine the indication $I_T$ of the thickness of the layer of the retina, the indication $I_T$ of the thickness of the layer of the retina may, more generally, be determined using a segmentation confidence map generated in any other way (hereinafter referred to as segmentation confidence map M'), which nevertheless indicates a spatial distribution, across the region of the retina, of a level of confidence in the retinal layer segmentation performed by a retinal layer segmentation algorithm. The segmentation confidence map M' may, as in the present example embodiment, comprise a two-dimensional array of segmentation confidence values that defines the aforementioned spatial distribution of the level of confidence in the retinal layer segmentation. The retinal layer segmentation algorithm may be any type of segmentation algorithm known to those skilled in the art that can perform retinal layer segmentation of an OCT scan of a portion of the retina, and need not be probabilistic in nature.

Figure 12:
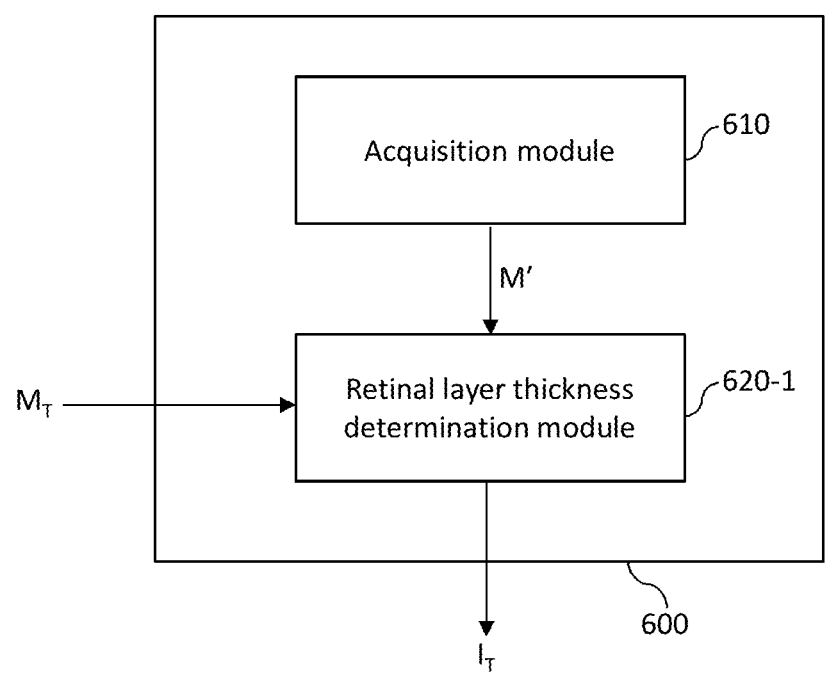
FIG. 12 is a schematic illustration of an apparatus for processing a retinal layer thickness map to determine an indication of a thickness of a layer of a retina according to a fifth example embodiment.

FIG. 12 is a schematic illustration of an apparatus 600 according to a fifth example embodiment for processing a retinal layer thickness map $M_T$, which indicates a spatial distribution of a thickness of a layer of a retina across a region of the retina and is based on a retinal layer segmentation of a volumetric OCT scan of a portion of the retina performed by the retinal layer segmentation algorithm of the general form described above, to determine an indication $I_T$ of the thickness of the layer of the retina. The retinal layer thickness map $M_T$ may, as in the present example embodiment, comprise a two-dimensional array of retinal layer thickness values that defines the aforementioned spatial distribution of the thickness of the layer of the retina across the region of the retina, wherein each retinal layer thickness value in the array has an associated (corresponding) segmentation confidence value in the segmentation confidence map which indicated a level of confidence in a result of the segmentation which has been used to calculate the retinal layer thickness value.

As shown in FIG. 12, the apparatus 600 comprises an acquisition module 610 and a retinal layer thickness determination module 620-1. The apparatus 600 may, as in the present example embodiment, be implemented in the form of a programmable signal processing hardware as described above with reference to FIG. 4. It should be noted, however, that one or both of the modules of the apparatus 600 may alternatively be implemented in non-programmable hardware, such as an ASIC.

The acquisition module 610 is arranged to acquire a segmentation confidence map M' indicating a spatial distribution, across the region of the retina, of a level of confidence in the retinal layer segmentation performed by the retinal layer segmentation algorithm. The segmentation confidence map M' may be generated by the acquisition module 610 using any of the techniques described above (or otherwise), or by the acquisition module 610 receiving the segmentation confidence map M' from a device external to the apparatus 600, as in the present example embodiment.

The retinal layer thickness map $M_T$ may be received by the apparatus 600 from a device external to the apparatus 600, as in the present example embodiment, or it may be generated by the retinal layer thickness determination module 620-1 using the retinal layer segmentation algorithm to segment a volumetric OCT scan of a portion of the retina.

The retinal layer thickness determination module 620-1 is arranged to determine the indication $I_T$ of the thickness of the layer of the retina using the retinal layer thickness map $M_T$ and the segmentation confidence map M'.

Figure 13:
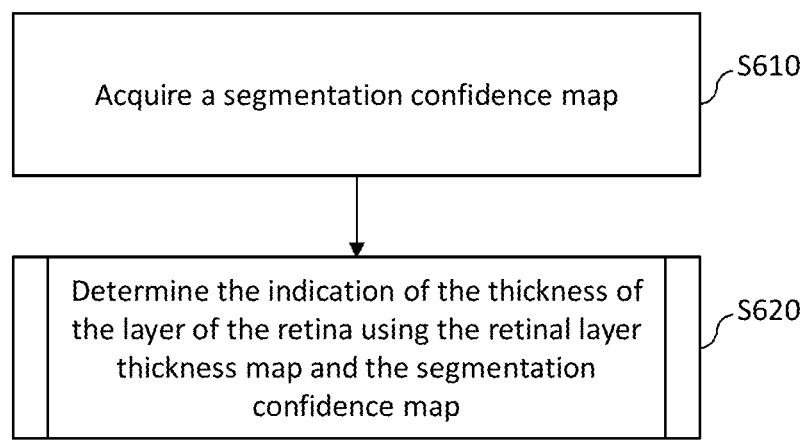
FIG. 13 is a flow diagram illustrating a method by which the apparatus of the fifth example embodiment processes the retinal layer thickness map to determine the indication of the thickness of the layer of the retina.

FIG. 13 is a flow diagram illustrating a method by which the apparatus 600 processes the retinal layer thickness map $M_T$ to determine the indication $I_T$ of the thickness of the layer of the retina.

In process S610 of FIG. 13, the acquisition module 610 acquires the segmentation confidence map M', by receiving it from an external device.

In process 5620 of FIG. 13, the retinal layer thickness determination module 620-1 determines the indication $I_T$ of the thickness of the layer of the retina using the retinal layer thickness map $M_T$ and the segmentation confidence map M'.

Figure 14:
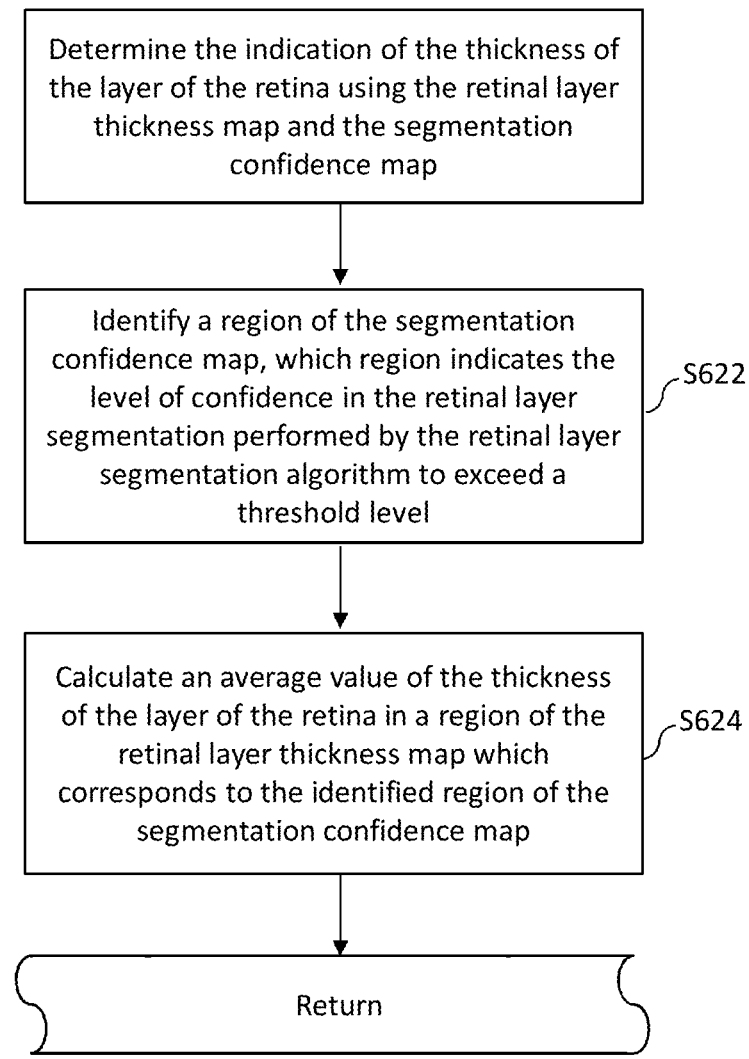
FIG. 14 is a flow diagram illustrating a process by which the retinal layer thickness determination module of the fifth example embodiment determines the indication of the thickness of the layer of the retina.

The retinal layer thickness determination module 620-1 may, as in the present example embodiment, be arranged to determine the indication $I_T$ of the thickness of the layer of the retina by the process illustrated in the flow diagram of FIG. 14, namely by identifying, in process 5622 of FIG. 14, a region of the segmentation confidence map M' (i.e. containing a set of values in the aforementioned array defining the segmentation confidence map M'), which region indicates the level of confidence in the retinal layer segmentation performed by the retinal layer segmentation algorithm to exceed a threshold confidence level $C_T$. The segmentation confidence values in the identified region thus all exceed the threshold confidence level $C_T$. In process 5624 of FIG. 14, the retinal layer thickness determination module 620-1 determines an average value (e.g. mean or median) of the thickness of the layer of the retina in a region of the retinal layer thickness map $M_T$ which corresponds to the identified region of the segmentation confidence map M'.

Figure 15:
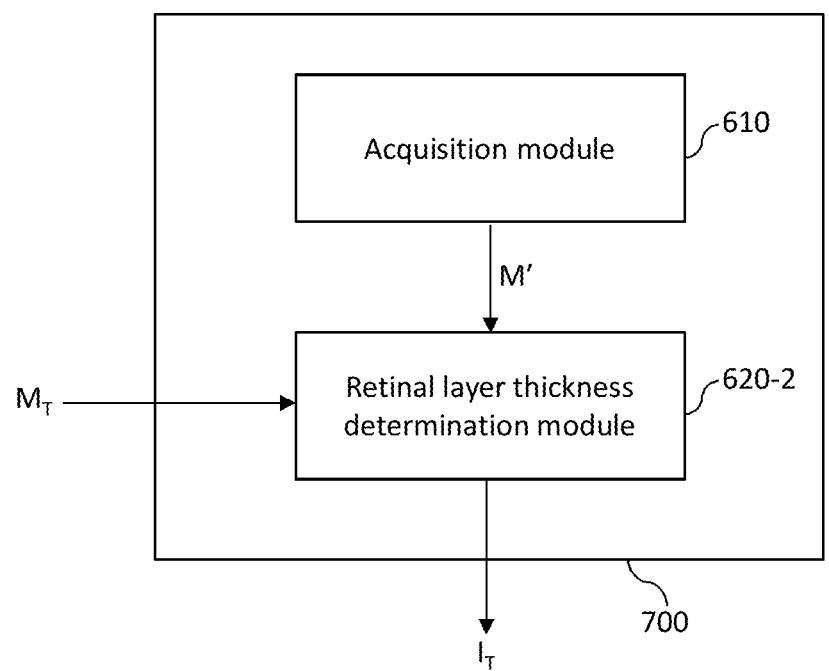
FIG. 15 is a schematic illustration of a variant of the apparatus of the fifth example embodiment.

FIG. 15 is a schematic illustration of an apparatus 700, which is a variant of apparatus 600 and is likewise arranged to process the retinal layer thickness map $M_T$ to determine an indication $I_T$ of the thickness of the layer of the retina. The apparatus 700 differs from apparatus 600 only by the functionality of the retinal layer thickness determination module 620-2, which is arranged to determine $I_T$ in a different way to the retinal layer thickness determination module 620-1. More particularly, the retinal layer thickness determination module 620-2 is arranged to determine the indication $I_T$ of the thickness of the layer of the retina by calculating a weighted average of the thickness of the layer of the retina in the region of the retina by weighting each thickness value indicated at a respective location in the retinal layer thickness map $M_T$ by the level of confidence indicated at a corresponding location in the segmentation confidence map M'.

The example aspects described here avoid limitations, specifically rooted in computer technology, relating to semantic segmentation of retinal OCT C-scans. In particular, probabilistic models used for semantic segmentation, which include (but are not limited to) convolutional neural network (CNN) models, provide segmentation results that can be difficult to interpret, owing to a lack of information on a level of confidence that can be placed on the segmentation results. By virtue of the example aspects described herein, probability information, which is used by segmentations model to perform semantic segmentation but then conventionally discarded, may be leveraged to provide an indication of a level of confidence in the segmentation results that can be used to enhance their interpretability, improve the reliability of retinal layer thickness measurements derived from the segmentation results, or provide metrics for logging OCT layer segmentation confidence, for example. Also, by virtue of the foregoing capabilities of the example aspects described herein, which are rooted in computer technology, the example aspects described herein improve computers and computer processing/functionality, and also improve the field(s) of at least retinal OCT image analysis.

There has been described, in accordance with example embodiments, an apparatus as set out in E1 to E16 below, and an apparatus as set out in E17 to E19 below, a computer-implemented method as set out in E20 to E22 below, and a non-transitory computer-readable storage medium as set out in E23 below.

E1. An apparatus for generating a segmentation confidence map by processing retinal layer segmentation data generated by a retinal layer segmentation algorithm, which generates, as the retinal layer segmentation data, a respective set of probability values for each voxel of at least a portion of a C-scan of a retina, wherein each probability value indicates a probability of the voxel belonging to a respective retinal layer class of a predefined set of retinal layer classes, the apparatus comprising:
a voxel classification module arranged to generate, for each voxel of a set of voxels for which the retinal layer segmentation data has been generated:
a respective value of a classification indicator based on the respective set of probability values, the value of the classification indicator indicating a classification of the voxel as belonging to a respective retinal layer class of the predefined set of retinal layer classes; and
a respective value of a first confidence indicator which is indicative of a respective level of confidence in the classification of the voxel;
a voxel identification module arranged to identify, for a retinal layer class of the predefined set of retinal layer classes, a subset of the set of voxels such that the value of the classification indicator generated for each voxel of the subset indicates a classification of the voxel as belonging to the retinal layer class;
a confidence evaluation module arranged to calculate, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and
a segmentation confidence map generation module arranged to generate the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

E2. The apparatus according to E1, wherein the voxel classification module is arranged to generate the respective value of the first confidence indicator for each voxel of the set of voxels for which the retinal layer segmentation data has been generated based on the respective set of probability values.

E3. The apparatus according to E2, wherein the voxel classification module is arranged to calculate the respective value of the first confidence indicator for each voxel of the set of voxels as one of:
a standard deviation of the respective set of probability values;
1−D, where D is a difference between a highest probability value in the respective set of probability values and a lowest probability value in the respective set of probability values; and
1−P, where P is a difference between a highest probability value in the respective set of probability values and a second highest probability value in the respective set of probability values.

E4. The apparatus according to any one of E1 to E3, wherein the retinal layer segmentation algorithm comprises one of a convolutional neural network, a Gaussian Mixture model, a Random Forest, a Bayesian classifier and a Support Vector Machine.

E5. The apparatus according to any one of E1 to E4, wherein
the retinal layer segmentation algorithm generates the retinal layer segmentation data by calculating, for each voxel of the at least a portion of the C-scan, a respective set of probability values, wherein each probability value indicates a probability of the voxel belonging to a respective class of a predefined set of classes, the predefined set of classes comprising the predefined set of retinal layer classes and a predefined background class,
the value of the classification indicator generated for each voxel of the set of voxels indicates a classification of the voxel as belonging to a respective class of the predefined set of classes,
the voxel identification module is arranged to identify, for the background class, a second subset of the set of voxels such that the value of the classification indicator generated for each voxel of the second subset indicates a classification of the voxel as belonging to the background class;
the confidence evaluation module is arranged to calculate, for each A-scan of a plurality of A-scans of the C-scan, which A-scan has at least one voxel in the identified second subset, a respective value of the second confidence indicator, based on at least one value of the first confidence indicator that has been respectively generated for the at least one voxel in the A-scan; and
the segmentation confidence map generation module is arranged to generate a second segmentation confidence map using the values of the second confidence indicator calculated for the A-scans having at least one voxel in the identified second subset, such that the second segmentation confidence map indicates a spatial distribution of a level of confidence in the classification of the voxels in the second subset as belonging to the background class.

E6. An apparatus for generating a segmentation confidence map by processing retinal layer segmentation data generated by a retinal layer segmentation algorithm, which generates the retinal layer segmentation data by generating, for each voxel of at least a portion of a C-scan of a retina, a respective value of a classification indicator indicating a classification of the voxel as belonging to a retinal layer class of the predefined set of retinal layer classes, the apparatus comprising:
a confidence indicator evaluation module arranged to generate, for each voxel of a set of voxels for which the retinal layer segmentation data has been generated, a respective value of a first confidence indicator which is indicative of a level of confidence in the classification of the voxel;
a voxel identification module arranged to identify, for a retinal layer class of the predefined set of retinal layer classes, a subset of the set of voxels such that the value of the classification indicator generated for each voxel of the subset indicates a classification of the voxel as belonging to the retinal layer class;
a confidence evaluation module arranged to calculate, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and
a segmentation confidence map generation module arranged to generate the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

E7. The apparatus according to any one of E1 to E6, wherein the voxel classification module is arranged to generate the respective value of the first confidence indicator for each voxel of the set of voxels for which the retinal layer segmentation data has been generated using a value of a local image quality metric that indicates an image quality of a region of an image, which region has been rendered from a part of the C-scan comprising the voxel.

E8. The apparatus according to any one of E1 to E7, further comprising a retinal layer thickness determination module arranged to us the segmentation confidence map and the values of the classification indicator to determine an indication of a thickness of a layer of the retina associated with the retinal layer class.

E9. The apparatus according to E8, wherein the retinal layer thickness determination module is arranged to determine the indication of the thickness of the layer of the retina by a process of:
using the segmentation confidence map to identify, in the plurality of A-scans, an A-scan for which the value of a second confidence indicator is indicative of a level of confidence in the classification of the at least one voxel in the A-scan into the retinal layer class that exceeds a predefined threshold; and
determining a count of the at least one voxel in the identified A-scan.

E10. The apparatus according to E9, wherein the retinal layer thickness determination module is arranged to repeat the process to:
identify, using the segmentation confidence map, a second plurality of A-scans in the plurality of A-scans, wherein the respective value of a second confidence indicator calculated for each A-scan of the second plurality of A-scans is indicative of a respective level of confidence in the classification of the at least one voxel in the A-scan into the retinal layer class that exceeds the predefined threshold; and
determine, for each A-scan of the identified second plurality of A-scans, a respective count of the at least one voxel in the A-scan,
wherein a respective indication of the thickness of the layer of the retina is determined for each predefined region of a plurality of predefined regions of the retina, from which predefined region a respective set of A-scans of the identified second plurality of A-scans has been acquired, by calculating an average of the counts determined for the A-scans of the set of A-scans.

E11. The apparatus according to E8, wherein retinal layer thickness determination module is arranged to determine the indication of the thickness of the layer of the retina by:
  determining, for each A-scan of the plurality of A-scans, which A-scan has at least one voxel in the identified subset, a respective count of the at least one voxel in the identified subset in the A-scan; and
  determining a weighted average of the determined counts, wherein the respective count determined for each A-scan having at least one voxel in the identified subset is weighted by the respective value of the second confidence indicator.

E12. The apparatus according to E11, wherein the retinal layer thickness determination module is arranged to determine the indication of the thickness of the layer of the retina for each predefined region of a plurality of predefined regions of the retina by:
  determining, for each A-scan acquired from the predefined region, which A-scan has at least one voxel in the identified subset, a respective count of the at least one voxel in the identified subset in the A-scan; and
  determining a weighted average of the determined counts, wherein the respective count determined for each A-scan acquired from the predefined region and having at least one voxel in the identified subset is weighted by the respective value of the second confidence indicator.

E13. The apparatus according to E10 or E12, wherein the predefined regions are demarcated by an ETDRS grid.

E14. The apparatus according to any one of E1 to E13, wherein the segmentation confidence map generation module is further arranged to generate image data defining an image of at least a portion of the segmentation confidence map, and to cause the image to be displayed on a display.

E15. The apparatus according to E14, wherein the segmentation confidence map generation module is arranged to cause the image to be displayed on the display as one of:
  an overlay on an en-face image displayed on the display, the en-face image being based on the subset of voxels classified as belonging to the retinal layer class;
  an overlay on a retinal layer thickness map displayed on the display, the retinal layer thickness map being based on the subset of voxels classified as belonging to the retinal layer class; and
  a plot aligned with a representation of a B-scan displayed on the display, the B-scan being based on the subset of voxels classified as belonging to the retinal layer class.

E16. The apparatus according to any one of E1 to E15, wherein the segmentation confidence map generation module is further arranged to determine whether the segmentation confidence map indicates a level of confidence in the classification of the voxels in the subset as belonging to the retinal layer class of the predefined set of retinal layer classes that is below a confidence threshold and, in a case where the segmentation confidence map is determined to indicate a level of confidence in the classification of the voxels that is below the confidence threshold, generate an alert for a user.

E17. An apparatus for processing a retinal layer thickness map, which indicates a spatial distribution of a thickness of a layer of a retina across a region of the retina and is based on a retinal layer segmentation of an optical coherence tomography scan of a portion of the retina performed by the retinal layer segmentation algorithm, to determine an indication of the thickness of the layer of the retina, the apparatus comprising:
  an acquisition module arranged to acquire a segmentation confidence map which indicates a spatial distribution, across the region of the retina, of a level of confidence in the retinal layer segmentation performed by the retinal layer segmentation algorithm; and
  a retinal layer thickness determination module arranged to determine the indication of the thickness of the layer of the retina using the retinal layer thickness map and the segmentation confidence map.

E18. The apparatus according to E17, wherein the retinal layer thickness determination module is arranged to determine the indication of the thickness of the layer of the retina by:
  identifying a region of the segmentation confidence map, which region indicates the level of confidence in the retinal layer segmentation performed by the retinal layer segmentation algorithm to exceed a threshold confidence level; and
  calculating an average value of the thickness of the layer of the retina in a region of the retinal layer thickness map which corresponds to the identified region of the segmentation confidence map.

E19. The apparatus according to E17, wherein the retinal layer thickness determination module is arranged to determine the indication of the thickness of the layer of the retina by:
  determining a weighted average of the thickness of the layer of the retina in the region of the retina by weighting each thickness value indicated at a respective location in the retinal layer thickness map by the level of confidence indicated at a corresponding location in the segmentation confidence map.

E20. A computer-implemented method of processing a retinal layer thickness map, which indicates a spatial distribution of a thickness of a layer of a retina across a region of the retina and is based on a retinal layer segmentation of an optical coherence tomography scan of a portion of the retina performed by the retinal layer segmentation algorithm, to determine an indication of the thickness of the layer of the retina, the method comprising:
  acquiring a segmentation confidence map which indicates a spatial distribution, across the region of the retina, of a level of confidence in the retinal layer segmentation performed by the retinal layer segmentation algorithm; and
  determine the indication of the thickness of the layer of the retina using the retinal layer thickness map and the segmentation confidence map.

E21. The computer-implemented method according to E20, wherein the indication of the thickness of the layer of the retina is determined by:
  identifying a region of the segmentation confidence map, which region indicates the level of confidence in the retinal layer segmentation performed by the retinal layer segmentation algorithm to exceed a threshold confidence level; and
  calculating an average value of the thickness of the layer of the retina in a region of the retinal layer thickness map which corresponds to the identified region of the segmentation confidence map.

E22. The computer-implemented method according to E20, wherein the indication of the thickness of the layer of the retina is determined by:
 determining a weighted average of the thickness of the layer of the retina in the region of the retina by weighting each thickness value indicated at a respective location in the retinal layer thickness map by the level of confidence indicated at a corresponding location in the segmentation confidence map.

E23. A non-transitory computer-readable storage medium storing computer program instructions which, when executed by a computer processor, cause the computer processor to perform the method according to at least one of E20 to E22.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g. program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects herein, as described above.

Included in the programming and/or software of the system are software modules for implementing the procedures described herein. In some example embodiments herein, a module includes software, although in other example embodiments herein, a module includes hardware, or a combination of hardware and software.

While various example embodiments have been described above, it should be understood that they have been presented by way of example, and not limitation. It will be apparent to persons skilled in the relevant art(s) that various changes in form and detail can be made therein. Thus, the present disclosure should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limiting, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

The invention claimed is:

1. A non-transitory computer-readable storage medium comprising computer program instructions which, when executed by at least one processor, cause the at least one processor to perform a method of generating a segmentation confidence map by processing retinal layer segmentation data generated by a retinal layer segmentation algorithm, which generates, as the retinal layer segmentation data, a respective set of probability values for each voxel of at least a portion of a C-scan of a retina, wherein each probability value indicates a probability of the voxel belonging to a respective retinal layer class of a predefined set of retinal layer classes, the method comprising:
  generating, for each voxel of a set of voxels for which the retinal layer segmentation data has been generated:
    a respective value of a classification indicator based on the respective set of probability values, the value of the classification indicator ($I_{class}$) indicating a classification of the voxel as belonging to a respective retinal layer class of the predefined set of retinal layer classes; and
    a respective value of a first confidence indicator which is indicative of a respective level of confidence in the classification of the voxel;
  identifying, for a retinal layer class of the predefined set of retinal layer classes, a subset of the set of voxels such that the value of the classification indicator generated for each voxel of the subset indicates a classification of the voxel as belonging to the retinal layer class;
  calculating, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and
  generating the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

2. The non-transitory computer-readable storage medium according to claim 1, wherein, in the generating of a respective value of the first confidence indicator for each voxel of the set of voxels, the respective value of the first confidence indicator is generated based on the respective set of probability values.

3. The non-transitory computer-readable storage medium according to claim 2, wherein the respective value of the first confidence indicator is calculated for each voxel of the set of voxels as one of:
  a standard deviation of the respective set of probability values;
  1−D, where D is a difference between a highest probability value in the respective set of probability values and a lowest probability value in the respective set of probability values; and
  1−P, where P is a difference between a highest probability value in the respective set of probability values and a second highest probability value in the respective set of probability values.

4. The non-transitory computer-readable storage medium according to claim 1, wherein the retinal layer segmentation algorithm comprises one of a convolutional neural network, a Gaussian Mixture model, a Random Forest, a Bayesian classifier and a Support Vector Machine.

5. The non-transitory computer-readable storage medium according to claim 1, wherein
  the retinal layer segmentation algorithm generates the retinal layer segmentation data by calculating, for each voxel of the at least a portion of the C-scan, a respective set of probability values, wherein each probability value indicates a probability of the voxel belonging to a respective class of a predefined set of classes, the predefined set of classes comprising the predefined set of retinal layer classes and a predefined background class,
  the value of the classification indicator generated for each voxel of the set of voxels indicates a classification of the voxel as belonging to a respective class of the predefined set of classes, and
  the method further comprises:
    for the background class, identifying a second subset of the set of voxels such that the value of the classification indicator generated for each voxel of the second subset indicates a classification of the voxel as belonging to the background class;
    calculating, for each A-scan of a plurality of A-scans of the C-scan, which A-scan has at least one voxel in the identified second subset, a respective value of the second confidence indicator, based on at least one value of the first confidence indicator that has been respectively generated for the at least one voxel in the A-scan; and
    generating a second segmentation confidence map using the values of the second confidence indicator calculated for the A-scans having at least one voxel in the identified second subset, such that the second segmentation confidence map indicates a spatial distribution of a level of confidence in the classification of the voxels in the second subset as belonging to the background class.

6. A non-transitory computer-readable storage medium comprising computer program instructions which, when executed by at least one processor, cause the at least one processor to perform a method of generating a segmentation confidence map by processing retinal layer segmentation data generated by a retinal layer segmentation algorithm, which generates the retinal layer segmentation data by calculating, for each voxel of at least a portion of a C-scan of a retina, a respective value of a classification indicator indicating a classification of the voxel as belonging to a retinal layer class of the predefined set of retinal layer classes, the method comprising:
  generating, for each voxel of a set of voxels for which the retinal layer segmentation data has been generated, a respective value of a first confidence indicator which is indicative of a level of confidence in the classification of the voxel;
  identifying, for a retinal layer class of the predefined set of retinal layer classes, a subset of the set of voxels such that the value of the classification indicator generated for each voxel of the subset indicates a classification of the voxel as belonging to the retinal layer class;
  calculating, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and
  generating the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

7. The non-transitory computer-readable storage medium according to claim 6, wherein, in the generating of a respective value of the first confidence indicator for each voxel of the set of voxels, the respective value of the first confidence indicator is generated using a value of a local image quality metric that indicates an image quality of a region of an image, which region has been rendered from a part of the C-scan comprising the voxel.

8. The non-transitory computer-readable storage medium according to claim 1, wherein the method further comprises using the segmentation confidence map and the values of the classification indicator to determine an indication of a thickness of a layer of the retina associated with the retinal layer class.

9. The non-transitory computer-readable storage medium according to claim 8, wherein the indication of the thickness of the layer of the retina is determined by a process of:
  using the segmentation confidence map to identify, in the plurality of A-scans, an A-scan for which the value of a second confidence indicator is indicative of a level of confidence in the classification of the at least one voxel in the A-scan into the retinal layer class that exceeds a predefined threshold; and
  determining a count of the at least one voxel in the identified A-scan.

10. The non-transitory computer-readable storage medium according to claim 9, wherein the process is repeated to:
  identify, using the segmentation confidence map, a second plurality of A-scans in the plurality of A-scans, wherein the respective value of a second confidence indicator calculated for each A-scan of the second plurality of A-scans is indicative of a respective level of confidence in the classification of the at least one voxel in the A-scan into the retinal layer class that exceeds the predefined threshold; and
  determine, for each A-scan of the identified second plurality of A-scans, a respective count of the at least one voxel in the A-scan,
  wherein a respective indication of the thickness of the layer of the retina is determined for each predefined region of a plurality of predefined regions of the retina, from which predefined region a respective set of A-scans of the identified second plurality of A-scans has been acquired, by calculating an average of the counts determined for the A-scans of the set of A-scans.

11. The non-transitory computer-readable storage medium according to claim 8, wherein the indication of the thickness of the layer of the retina is determined by:
  determining, for each A-scan of the plurality of A-scans, which A-scan has at least one voxel in the identified subset, a respective count of the at least one voxel in the identified subset in the A-scan; and
  determining a weighted average of the determined counts, wherein the respective count determined for each A-scan having at least one voxel in the identified subset is weighted by the respective value of the second confidence indicator.

12. The non-transitory computer-readable storage medium according to claim 11, wherein the indication of the thickness of the layer of the retina is determined for each predefined region of a plurality of predefined regions of the retina by:
  determining, for each A-scan acquired from the predefined region, which A-scan has at least one voxel in the identified subset, a respective count of the at least one voxel in the identified subset in the A-scan; and
  determining a weighted average of the determined counts, wherein the respective count determined for each A-scan acquired from the predefined region and having at least one voxel in the identified subset is weighted by the respective value of the second confidence indicator.

13. The non-transitory computer-readable storage medium according to claim 10, wherein the predefined regions are demarcated by an ETDRS grid.

14. The non-transitory computer-readable storage medium according to claim 1, wherein the method further comprises generating image data defining an image of at least a portion of the segmentation confidence map, and causing the image to be displayed on a display.

15. The non-transitory computer-readable storage medium according to claim 14, wherein the image is caused to be displayed on the display as one of:
  an overlay on an en-face image displayed on the display, the en-face image being based on the subset of voxels classified as belonging to the retinal layer class;
  an overlay on a retinal layer thickness map displayed on the display, the retinal layer thickness map being based on the subset of voxels classified as belonging to the retinal layer class; and
  a plot aligned with a representation of a B-scan displayed on the display, the B-scan being based on the subset of voxels classified as belonging to the retinal layer class.

16. The non-transitory computer-readable storage medium according to claim 1, wherein the method further comprises:
  determining whether the segmentation confidence map indicates a level of confidence in the classification of the voxels in the subset as belonging to the retinal layer class of the predefined set of retinal layer classes that is below a confidence threshold and, in a case where the segmentation confidence map is determined to indicate a level of confidence in the classification of the voxels that is below the confidence threshold, generating an alert for a user.

17. An apparatus for generating a segmentation confidence map by processing retinal layer segmentation data generated by a retinal layer segmentation algorithm, which generates, as the retinal layer segmentation data, a respective set of probability values for each voxel of at least a portion of a C-scan of a retina, wherein each probability value indicates a probability of the voxel belonging to a respective retinal layer class of a predefined set of retinal layer classes, the apparatus comprising:
- a voxel classification module arranged to generate, for each voxel of a set of voxels for which the retinal layer segmentation data has been generated:
  - a respective value of a classification indicator based on the respective set of probability values, the value of the classification indicator indicating a classification of the voxel as belonging to a respective retinal layer class of the predefined set of retinal layer classes; and
  - a respective value of a first confidence indicator which is indicative of a respective level of confidence in the classification of the voxel;
- a voxel identification module arranged to identify, for a retinal layer class of the predefined set of retinal layer classes, a subset of the set of voxels such that the value of the classification indicator generated for each voxel of the subset indicates a classification of the voxel as belonging to the retinal layer class;
- a confidence evaluation module arranged to calculate, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and
- a segmentation confidence map generation module arranged to generate the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

18. An apparatus for generating a segmentation confidence map by processing retinal layer segmentation data generated by a retinal layer segmentation algorithm, which generates the retinal layer segmentation data by generating, for each voxel of at least a portion of a C-scan of a retina, a respective value of a classification indicator indicating a classification of the voxel as belonging to a retinal layer class of the predefined set of retinal layer classes, the apparatus comprising:
- a confidence indicator evaluation module arranged to generate, for each voxel of a set of voxels for which the retinal layer segmentation data has been generated, a respective value of a first confidence indicator which is indicative of a level of confidence in the classification of the voxel;
- a voxel identification module arranged to identify, for a retinal layer class of the predefined set of retinal layer classes, a subset of the set of voxels such that the value of the classification indicator generated for each voxel of the subset indicates a classification of the voxel as belonging to the retinal layer class;
- a confidence evaluation module arranged to calculate, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and
- a segmentation confidence map generation module arranged to generate the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

19. The non-transitory computer-readable storage medium according to claim 6, wherein the method further comprises using the segmentation confidence map and the values of the classification indicator to determine an indication of a thickness of a layer of the retina associated with the retinal layer class.

20. The non-transitory computer-readable storage medium according to claim 19, wherein the indication of the thickness of the layer of the retina is determined by a process of:
- using the segmentation confidence map to identify, in the plurality of A-scans, an A-scan for which the value of a second confidence indicator is indicative of a level of confidence in the classification of the at least one voxel in the A-scan into the retinal layer class that exceeds a predefined threshold; and
- determining a count of the at least one voxel in the identified A-scan.

21. The non-transitory computer-readable storage medium according to claim 19, wherein the indication of the thickness of the layer of the retina is determined by:
- determining, for each A-scan of the plurality of A-scans, which A-scan has at least one voxel in the identified subset, a respective count of the at least one voxel in the identified subset in the A-scan; and
- determining a weighted average of the determined counts, wherein the respective count determined for each A-scan having at least one voxel in the identified subset is weighted by the respective value of the second confidence indicator.

22. The non-transitory computer-readable storage medium according to claim 6, wherein the method further comprises generating image data defining an image of at least a portion of the segmentation confidence map, and causing the image to be displayed on a display,
wherein the image is caused to be displayed on the display as one of:
- an overlay on an en-face image displayed on the display, the en-face image being based on the subset of voxels classified as belonging to the retinal layer class;
- an overlay on a retinal layer thickness map displayed on the display, the retinal layer thickness map being based on the subset of voxels classified as belonging to the retinal layer class; and
- a plot aligned with a representation of a B-scan displayed on the display, the B-scan being based on the subset of voxels classified as belonging to the retinal layer class.

23. The non-transitory computer-readable storage medium according to claim 6, wherein the method further comprises:
- determining whether the segmentation confidence map indicates a level of confidence in the classification of the voxels in the subset as belonging to the retinal layer class of the predefined set of retinal layer classes that is below a confidence threshold and, in a case where the segmentation confidence map is determined to indicate a level of confidence in the classification of the voxels that is below the confidence threshold, generating an alert for a user.

24. A method of generating a segmentation confidence map by processing retinal layer segmentation data generated by a retinal layer segmentation algorithm, which generates, as the retinal layer segmentation data, a respective set of probability values for each voxel of at least a portion of a C-scan of a retina, wherein each probability value indicates a probability of the voxel belonging to a respective retinal layer class of a predefined set of retinal layer classes, the method comprising:
- generating, for each voxel of a set of voxels for which the retinal layer segmentation data has been generated:
  - a respective value of a classification indicator based on the respective set of probability values, the value of the classification indicator ($I_{class}$) indicating a classification of the voxel as belonging to a respective retinal layer class of the predefined set of retinal layer classes; and
  - a respective value of a first confidence indicator which is indicative of a respective level of confidence in the classification of the voxel;
- identifying, for a retinal layer class of the predefined set of retinal layer classes, a subset of the set of voxels such that the value of the classification indicator generated for each voxel of the subset indicates a classification of the voxel as belonging to the retinal layer class;
- calculating, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and
- generating the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

25. A method of generating a segmentation confidence map by processing retinal layer segmentation data generated by a retinal layer segmentation algorithm, which generates the retinal layer segmentation data by calculating, for each voxel of at least a portion of a C-scan of a retina, a respective value of a classification indicator indicating a classification of the voxel as belonging to a retinal layer class of the predefined set of retinal layer classes, the method comprising:
- generating, for each voxel of a set of voxels for which the retinal layer segmentation data has been generated, a respective value of a first confidence indicator which is indicative of a level of confidence in the classification of the voxel;
- identifying, for a retinal layer class of the predefined set of retinal layer classes, a subset of the set of voxels such that the value of the classification indicator generated for each voxel of the subset indicates a classification of the voxel as belonging to the retinal layer class;
- calculating, for each A-scan of a plurality of A-scans of the C-scan, which A-scan has at least one voxel in the identified subset, a respective value of a second confidence indicator which is indicative of a level of confidence in a classification of the at least one voxel in the A-scan into the retinal layer class, based on at least one value of the first confidence indicator that has been respectively generated for the at least one voxel in the A-scan; and
- generating the segmentation confidence map using the calculated values of the second confidence indicator, such that the segmentation confidence map indicates a spatial distribution of a level of confidence in the classification of the voxels in the subset as belonging to the retinal layer class of the predefined set of retinal layer classes.

* * * * *